United States Patent
Sood et al.

(10) Patent No.: US 10,014,561 B2
(45) Date of Patent: Jul. 3, 2018

(54) SYSTEMS, METHODS, AND DEVICES FOR HEALTH MONITORING OF AN ENERGY STORAGE DEVICE

(71) Applicant: UNIVERSITY OF MARYLAND, COLLEGE PARK, College Park, MD (US)

(72) Inventors: Bhanu Sood, Gaithersburg, MD (US); Michael G. Pecht, Hyattsville, MD (US); Michael D. Osterman, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/912,113

(22) PCT Filed: Aug. 14, 2014

(86) PCT No.: PCT/US2014/051013
§ 371 (c)(1),
(2) Date: Feb. 15, 2016

(87) PCT Pub. No.: WO2015/023820
PCT Pub. Date: Feb. 19, 2015

(65) Prior Publication Data
US 2016/0197382 A1 Jul. 7, 2016

Related U.S. Application Data

(60) Provisional application No. 61/866,300, filed on Aug. 15, 2013.

(51) Int. Cl.
*G01N 29/07* (2006.01)
*H01M 10/42* (2006.01)
(Continued)

(52) U.S. Cl.
CPC ........... *H01M 10/4257* (2013.01); *B60L 3/12* (2013.01); *B60L 11/1857* (2013.01);
(Continued)

(58) Field of Classification Search
CPC ...... G01N 29/043; G01N 29/07; G01N 29/43; G01N 2291/0231; G01N 2291/2698
(Continued)

(56) References Cited

U.S. PATENT DOCUMENTS 4,337,661 A * 7/1982 Kretz ................. A61B 8/00
600/440
4,442,700 A * 4/1984 Swoboda ............. G01N 9/24
73/32 A (Continued)

OTHER PUBLICATIONS

Balbuena et al., Table of Contents and Preface for *Lithium-Ion Batteries: Solid-Electrolyte Interphase*, Imperial College Press, London, UK, 2004.
(Continued)

*Primary Examiner* — Manish S Shah
*Assistant Examiner* — Rose M Miller
(74) *Attorney, Agent, or Firm* — Shapiro, Gabor and Rosenberger, PLLC

(57) ABSTRACT

A health monitoring device includes an ultrasound source and an ultrasound sensor. The ultrasound source can be configured to generate and direct ultrasound at an energy storage device. The ultrasound sensor can be configured to detect ultrasound reflected from or transmitted through the energy storage device and to generate a signal responsive to the detected ultrasound from the energy storage device. A control unit can be configured to determine a state of health of the energy storage device based on the signal from the ultrasound sensor.

13 Claims, 8 Drawing Sheets

(51) Int. Cl.
G01N 29/04 (2006.01)
G01R 31/36 (2006.01)
B60L 3/12 (2006.01)
B60L 11/18 (2006.01)
H01M 10/0525 (2010.01)
G01N 29/11 (2006.01)
G01N 29/26 (2006.01)
H01M 10/48 (2006.01)

(52) U.S. Cl.
CPC ........ *B60L 11/1864* (2013.01); *G01N 29/043* (2013.01); *G01N 29/07* (2013.01); *G01N 29/11* (2013.01); *G01N 29/26* (2013.01); *G01R 31/3679* (2013.01); *H01M 10/0525* (2013.01); *H01M 10/4207* (2013.01); *H01M 10/4285* (2013.01); *H01M 10/48* (2013.01); *B60L 2240/545* (2013.01); *B60L 2240/547* (2013.01); *B60L 2240/549* (2013.01); *B60L 2250/10* (2013.01); *H01M 2010/4271* (2013.01); *H01M 2010/4278* (2013.01); *H01M 2220/20* (2013.01); *Y02E 60/122* (2013.01); *Y02T 10/7011* (2013.01); *Y02T 10/7061* (2013.01)

(58) Field of Classification Search
USPC .................. 73/602, 579, 582, 597, 598, 627
See application file for complete search history.

(56) References Cited

U.S. PATENT DOCUMENTS

| | | | | |
|---|---|---|---|---|
| 5,750,895 | A * | 5/1998 | Chern ................. | G01N 29/0609 73/614 |
| 6,520,018 | B1 * | 2/2003 | Flores-Lira ............ | G01N 29/11 73/629 |
| 8,104,341 | B2 | 1/2012 | Lagergren et al. | |
| 8,231,533 | B2 | 7/2012 | Buchalter | |
| 2008/0028860 | A1 * | 2/2008 | Refko ...................... | G01H 1/16 73/597 |
| 2008/0133156 | A1 * | 6/2008 | Redko ............... | H01M 10/4285 702/63 |
| 2011/0030477 | A1 | 2/2011 | Cousins | |
| 2011/0183168 | A1 | 7/2011 | Johnnie et al. | |
| 2012/0135337 | A1 * | 5/2012 | Herchen ................ | G01N 21/95 429/535 |
| 2012/0148880 | A1 * | 6/2012 | Schaefer ............... | H01M 10/48 429/50 |
| 2012/0283605 | A1 | 11/2012 | Lewis, Jr. | |
| 2013/0269436 | A1 * | 10/2013 | Couse .................... | G01N 29/12 73/582 |
| 2013/0302655 | A1 | 11/2013 | Deveau et al. | |
| 2016/0084911 | A1 * | 3/2016 | Mensah-Brown . | G01R 31/3606 318/139 |
| 2016/0141732 | A1 * | 5/2016 | Kuhne .................. | G01F 23/296 429/50 |
| 2016/0223498 | A1 * | 8/2016 | Steingart ............ | G01N 29/4427 |

OTHER PUBLICATIONS

Bluemtech webpage for WaterGel Ultrasound Solid Gel Pad [retrieved Jul. 8, 2014]. Retrieved from the Internet: <URL: http://bluemtech.en.ec21.com/Ultrasound_Solid_Gel_Pad_-WATERGEL---8129413_8129732.html>.
Ginzel et al., "Ultrasonic properties of a new low attenuation dry couplant elastomer," Ginzel Brothers & Associates Ltd., Apr. 1994.
Goldman et al., "Strain anisotropies and self-limiting capacities in single-crystalline 3D silicon microstructures: Models for high energy density lithium-ion battery anodes," *Advanced Functional Materials*, 2011, 21(13): pp. 2412-2422.
International Search Report and Written Opinion, dated Nov. 13, 2014, for International Application No. PCT/US14/51013.
Klucinec, B., "The Effectiveness of the Aquaflex Gel Pad in the Transmission of Acoustic Energy," Journal of Athletic Training, Dec. 1996, 31(4): pp. 313-317.
Kumai et al., "Gas generation mechanism due to electrolyte decomposition in commercial lithium-ion cell," *Journal of Power Sources*, 1999, 81-82: pp. 715-719.
Med-Electronics listing for Parker Laboratories AquaFlex Ultrasound Gel Pad [retrieved Jul. 8, 2014]. Retrieved from the Internet: <URL: http://www.med-electronics.com/Parker-Laboratories-AquaFlex-Ultrasound-Gel-Pad-p/pli-aquaflex.htm>.
Meissner et al., "Battery monitoring and electrical energy management precondition for future vehicle electric power systems," *Journal of Power Sources*, 2003, 116(1): pp. 79-98.
Ng et al., "Enhanced coulomb couting method for estimating state-of-charge and state-of-health of lithium-ion batteries," *Applied Energy*, 2009, 86(9): pp. 1506-1511.
Ohsaki et al., "Overcharge reaction of lithium-ion batteries," *Journal of Power Sources*, 2005, 146(1): pp. 97-100.
Plett, G.L., "Extended Kalman filtering for battery management systems of LiPB-based HEV battery packs, Part 3. State and parameter estimation," *Journal of Power Sources*, 2004, 134(2): pp. 277-292.
Pop et al., "State-of-the-art of battery state-of-charge determination," *Measurement Science and Technology*, 2005, 16(12): pp. R93-110.
Selfridge, A.R., "Approximate material properties in isotropic materials," *IEEE Transactions on Sonics and Ultrasonics*, May 1985, SU-32(3): pp. 381-394.
Sood et al., "Health monitoring of lithium-ion batteries," *Electronic Device Failure Analysis*, 2014, 2: pp. 4-14.
Sood et al., "Lithium-ion battery degradation mechanims and failure analysis methodology," *ISTFA 2012: Conference Proceedins from the 38th International Symposium for Testing and Failure Analysis*, Nov. 2012, pp. 239-249.
Williard et al., "Disassembly methodology for conducting failure analysis on lithium-ion batteries," *J. Mater. Sci.: Mater. Electron.*, 2011, 22(10): pp. 1616-1630.
Xing et al., "Battery management systems in electric and hybrid vehicles," *Energies*, 2011, 4(11): pp. 1840-1857.
Zimmerman, A.H., "Self-discharge losses in lithium-ion cells," *IEEE Aerospace and Electronic Systems*, 2004, pp. 19-24.

* cited by examiner

SYSTEMS, METHODS, AND DEVICES FOR HEALTH MONITORING OF AN ENERGY STORAGE DEVICE

CROSS-REFERENCE TO RELATED APPLICATIONS

The present application claims the benefit of U.S. Provisional Application No. 61/866,300, filed Aug. 15, 2013, which is hereby incorporated by reference herein in its entirety.

FIELD

The present disclosure relates generally to health monitoring of an energy storage device, and, more particularly, to ultrasonic assessment of lithium-ion battery cells to monitor a state of health.

SUMMARY

Systems, methods, and devices for monitoring a state of health of an energy storage device, such as a lithium-ion battery cell, are disclosed herein. In general, an ultrasonic acoustic source and sensor can be disposed proximal to a surface of a battery cell, which may be part of a larger battery pack. The ultrasonic source and sensor can be used to nondestructively assess the internal condition of vital interfaces inside the battery cell. These interfaces can include the interface between the anode active material, the cathode material, and the respective current collector (e.g., a metallic current collector). Alternatively or additionally, the ultrasonic source and sensor can be used to monitor battery swelling, electrode expansion, and/or electrode ruffling among other things. The resulting information can used to determine a state of health of the battery cell and/or the battery pack. The information about the extent of degradation can be used for predicting the reliability and/or the remaining useful life of the battery cell and/or battery pack.

In one or more embodiments of the disclosed subject matter, a health monitoring device comprises an ultrasound source and an ultrasound sensor. The ultrasound source is configured to generate and direct ultrasound at an energy storage device. The ultrasound sensor is configured to detect ultrasound reflected from or transmitted through the energy storage device and to generate a signal responsive to the detected ultrasound from the energy storage device.

In one or more embodiments of the disclosed subject matter, a method of monitoring an energy storage device comprises applying ultrasound to an energy storage device and detecting ultrasound reflected from or transmitted through the energy storage device. The method further comprises generating a signal indicative of the detected ultrasound.

In one or more embodiments of the disclosed subject matter, a battery system with state of health monitoring comprises a battery pack, one or more ultrasonic health monitoring devices, and a battery management system. The battery pack comprises a plurality of individual lithium-ion battery cells. Each ultrasonic health monitoring device is arranged to assess one of the lithium-ion battery cells and includes an ultrasound source that directs ultrasound at the respective lithium-ion battery cell. Each ultrasonic health monitoring device further includes an ultrasound sensor that detects ultrasound reflected from or transmitted through the respective lithium-ion battery cell and generates a signal responsive thereto. The battery management system is configured to receive the signal from each ultrasound sensor and to determine a state of health of the battery pack based at least in part on said signal.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

DETAILED DESCRIPTION

Figure 1A:
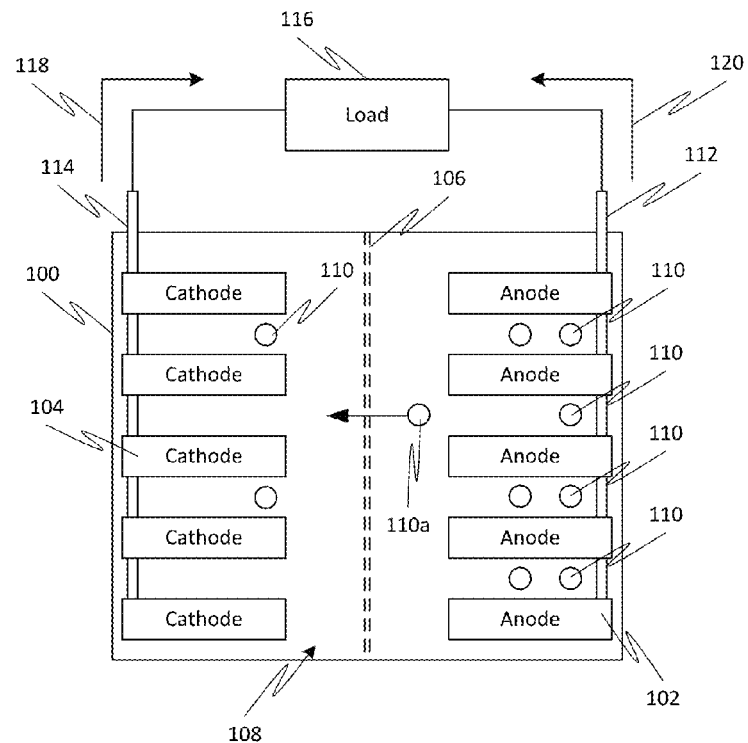
FIG. 1A is a simplified conceptual illustration of discharging of a lithium-ion battery.

In one or more embodiments of the disclosed subject matter, an energy storage device, such as a battery cell (e.g., a lithium-ion battery cell), can be non-destructively assessed using ultrasound in order to determine a state of health or other information regarding the interior structure of the energy storage device. In some embodiments, the ultrasonic assessment may occur while the energy storage device is in use (e.g., during charging or discharging of the battery cell) so as to provide real-time information regarding the state of health of the energy storage device in the field. Control or use of the energy storage device may be altered in response to the real-time information, for example, to take corrective action to address imminent failure of the energy storage device. Alternatively or additionally, the information can be used to predict reliability or determine the remaining useful life of a system incorporating the energy storage device, for example, a battery pack with multiple battery cells. In other embodiments, the ultrasonic assessment may occur when the energy storage device is not yet in service, for example, as part of a field return evaluation or manufacturing quality control. In any of the embodiments, health monitoring can be accomplished by monitoring confidence values computed by applying statistical pattern recognition techniques to the transient behavior of battery cells, transient responses, and correlation of the responses with models and validated with experimental data.

To perform the ultrasonic assessment of the energy storage device, ultrasonic pulses generated by an ultrasound source (e.g., an ultrasound pulser or transducer) can be focused at specific depths within the energy storage device to be assessed. As the acoustic wave approaches an interface within the energy storage device, the acoustic wave may be partially or totally reflected. Such interfaces may be associated with changes in the internal volume of the energy storage device caused by delamination, voiding, or other phenomena. The intensity of the reflected wave and/or transmitted wave is a function of the acoustic impedance of the interface. The reflected and/or transmitted waves can thus provide a measure of changes in the internal structure of the energy storage device that may be indicative of imminent failure or increasing degradation.

Lithium Ion Batteries

In one or more embodiments of the disclosed subject matter, the energy storage device is a battery cell, for example, a lithium-ion battery cell. Lithium-ion battery cells are free of many of the deficiencies from which other rechargeable battery cells suffer, such as high self-discharge rates and memory effects due to partial charge and discharge. In addition, because of their high energy density, long cycle life, and battery cell voltage, lithium-ion cells have been adopted for use in portable electronics as well as automotive applications, for example, as an energy storage device for all-electric or hybrid vehicles.

Figure 1B:
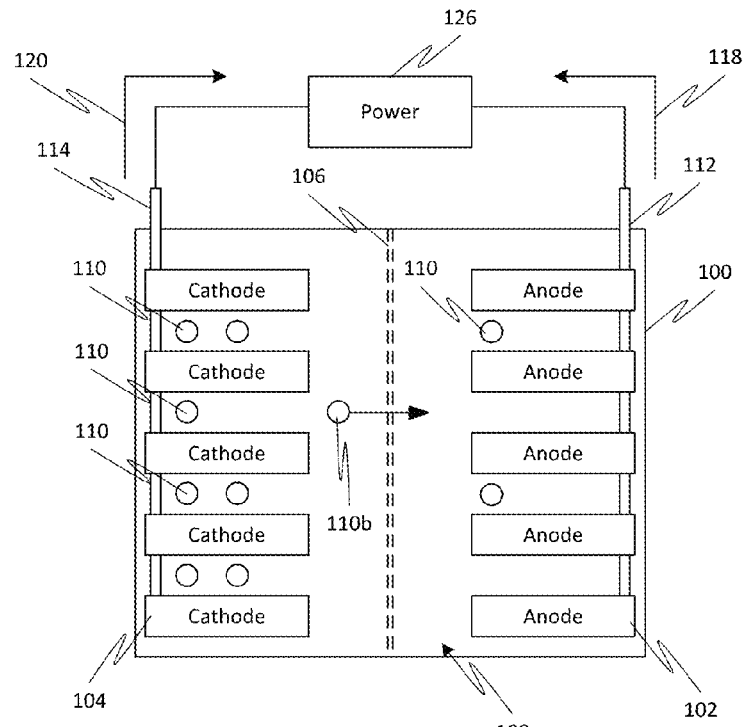
FIG. 1B is a simplified conceptual illustration of charging of a lithium-ion battery.

FIGS. 1A-1B are schematic diagrams of discharging and charging configurations, respectively, to illustrate various structures associated with a lithium-ion battery cell 100. In general, a lithium-ion battery cell 100 can include one or more cathode layers 104, one or more anode layers 102, respective current collectors on which the layers 102, 104 are disposed, a separator 106, and electrolytes 108 filling the interior volume of the battery cell 100. The electrolytes 108 can include a mixture of organic carbonate solvents (e.g., ethylene carbonate and dimethyl carbonate) and polymer salts (e.g., $LiPF_6$), which provide conductivity for the transport of lithium ions 110 between the electrodes 102, 104. Electrical contact between the internal electrodes 102, 104 is made via anode terminal 112 and cathode terminal 114, respectively, which are disposed external to the interior volume of the battery cell.

During the charging process (FIG. 1B), a current 118 is supplied to the cathode terminal 114 via a charging power source 126. Electron flow 120 is from the cathode terminal 114 to the charging power source 126. The cathode 104 has a high standard redox potential. As a result the current 118 and electron flow 120, the transition metal of the cathode 104 is oxidized and lithium ions 110b diffuse through the separator 106 to the anode 102, where they are intercalated into layers of, for example, carbon graphite to form $Li_xC_6$.

During the discharging process (FIG. 1A), a load 116 is connected between the cathode terminal 114 and the anode terminal 112. As a result, the electron flow 120 is from the anode terminal 112 to the cathode terminal 114 while the current 118 is in the opposite direction. As a result, the transition metal of the cathode 104 is reduced. In addition, lithium ions 110a are deintercalated from the anode 102 and move though the electrolyte 108 and the separator 106 back to the cathode 104.

Figure 2A:
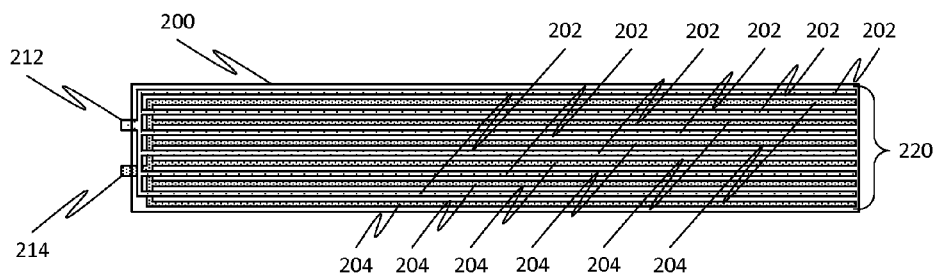
FIG. 2A is a diagram illustrating an internal arrangement of interdigitated electrode layers within an example of a battery cell.

It is to be appreciated that FIGS. 1A-1B are simplified illustrations of the inner workings of a lithium-ion battery cell and that practical embodiments of a lithium-ion battery cell will include more complex arrangements than those illustrated. For example, the cathode and electrode layers can be arranged in an interdigitated fashion, with alternating layers of anode and cathode electrodes in a thickness direction of the battery cell. Such a battery cell 200 is illustrated schematically in FIG. 2A. Thus, the anode layers 202 are arranged between adjacent cathode layers 204, and vice versa. Each anode layer 202 and each cathode layer 204 may be connected (in parallel or in series) to the anode terminal 212 and the cathode terminal 214, respectively, which provides electrical connection to a load or charging device located external to the battery cell. A separator layer (not shown) is provided between each adjacent cathode 204 and anode 202. The multi-layered electrode separator structure 220 sits in an electrolyte solution within an interior volume of the battery cell 200 and operates in a similar manner as described above with respect to FIGS. 1A-1B.

For simplicity of illustration and explanation, the electrodes and separator (including their arrangement and number) in the following drawings have been simplified as a number of parallel lines and referred to generally as 220. However, other arrangements and configurations for the structure of the battery cell beyond those specifically illustrated and discussed are also possible according to one or more contemplated embodiments. For example, the battery cell may have a so-called button configuration. In the button configuration, the battery cell may be substantially cylindrical with a top surface of the cylinder serving as one electrode terminal and a bottom surface of the cylinder serving as the other electrode terminal. The electrode layers within the button cell can be arranged perpendicular to an axis of the button cell, as annular layers extending along the axis of the button cell, or in any other arrangement. In another contemplated embodiment, the battery cell need not have clearly delineated electrode layers within the interior volume thereof. For example, the interior volume of the battery cell may be filled with a slurry and electrode terminals can extend into the interior volume to provide electrical contact thereto. In another example, the interior volume of the battery cell may comprise lumps of material rather than planar electrodes. Such configurations may suffer from similar degradation as the planar electrode configurations discussed above. One of ordinary skill in the art will appreciate that other battery cell configurations are also possible and will benefit from assessment using the disclosed ultrasonic health monitoring devices and techniques.

Despite advances in materials, packaging technologies and state monitoring solutions, many challenges regarding reliable use of lithium-ion battery cells remain. Over the lifecycle of a lithium-ion battery cell, various thermal, mechanical, and electrochemical processes contribute to the degradation of the cell's performance. Lithium-ion batteries generally begin to degrade almost immediately after completion of manufacturing and continue to degrade during storage and use. Degradation due to self-discharge, which occurs during storage as well as during charge/discharge cycling, may depend on the ambient temperature, storage time, and the state of charge of the cell (e.g., fully charged, partially charged, fully discharged, etc.). Additional degradation during charge/discharge cycles can be accelerated based on high-temperature exposure, frequent charge/discharge cycles, deep discharge (i.e., approaching fully discharged before recharging), and overcharge (i.e., charging beyond a designated capacity of the battery cell).

Vital interfaces where degradation may occur inside a lithium-ion battery cell include the interface between the metallic current collector and the active material for both the anode and cathode. Internal resistance can increase with complex chemical reactions between the active materials, electrodes, and the electrolyte. Battery materials may also be susceptible to expansion during charging. As a result, the anode or cathode layers within the battery cell may delaminate from their respective current collector, thereby causing a shift in charge and discharge properties of the battery.

Figure 2B:
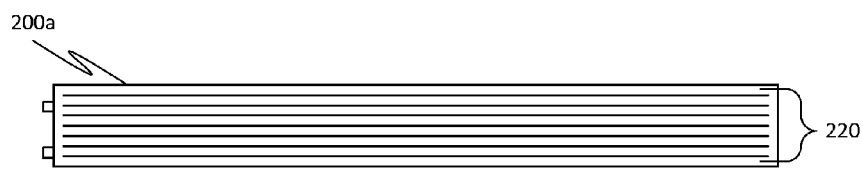
FIG. 2B is a simplified diagram of a battery cell in an as-manufactured state of health.

FIG. 2B depicts a battery cell 200a in an as-manufactured state. Battery cell 200a thus has a set initial thickness and an ordered arrangement of electrode layers 220 within the internal volume of the battery cell. However, with continued charge and discharge cycles, swelling, delamination, or other degradation can occur.

Figure 2C:
FIG. 2C is a simplified diagram of a battery cell deviating from a manufactured state of health due to ruffling of the electrode layers.

FIG. 2C shows a battery cell 200b that has degraded after multiple charging/discharging cycles. In particular, the electrode layers 220 have deformed resulting in electrode ruffling. Volumetric expansion of the electrode particles can cause localized stress concentrations that ruffle the electrode. This can cause a loss of connectivity between the electrode active material particles and the electrically conductive particles included in the electrode matrix. Separation or delamination of the electrode material and the current collector can occur. As a result, the useful capacity of the battery cell decreases due to its reduced charge-transfer capabilities.

Figure 2D:
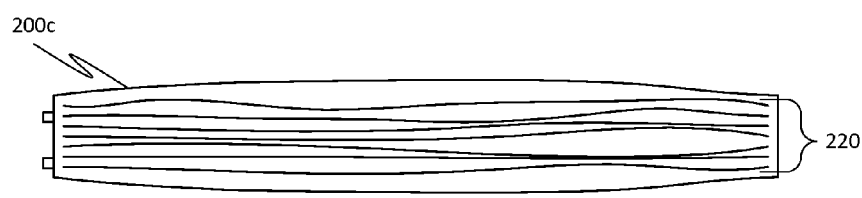
FIG. 2D is a simplified diagram of a battery cell deviating from a manufactured state of health due to swelling and ruffling of the electrode layers.
Figure 2E:
FIG. 2E is a simplified diagram of a battery cell deviating from a manufactured state of health due to swelling.

FIG. 2D shows another battery cell 200c that has degraded after multiple charging/discharging cycles. For example, localized heating and abusive operating conditions can result in the release of gas species that can cause volumetric expansion and/or venting of the cell to relieve internal pressure. If the battery cell is overcharged, the cathode can become unstable and the electrolyte can decompose. Alternatively or additionally, if the battery cell is overdischarged, the current collector (e.g., made of copper) can dissolve and cause internal short circuiting. As a result, local hotspots within the cell may be created that cause a variety of chemical reactions that release gas as a byproduct. The gas release can cause ruffling of the electrode layers 220, similar to that illustrated in FIG. 2C, and may further cause a swelling of a housing of the battery cell 200c, thereby resulting a change in thickness of the battery cell 200c and/or localized deformation of one or more surfaces of the housing of the battery cell 200c. In some cases, swelling of the housing of the battery cell 200d may be present without significant ruffling of the electrode layer 220, as illustrated schematically in FIG. 2E.

In worst case scenarios, rapidly increasing temperatures and excessive gas generation can cause the cell to explode and catch fire. However, many cells exhibit less severe levels of gas generation over their lifetime. This gas generation contributes to internal structural changes to the cell that can degrade the battery over its life cycle. For example, gas pockets in cycled cells can lead to a degradation due to displacement of the electrodes, thereby making it more difficult to transport ions through the electrolyte. Additionally, porosity in the electrode can increase thereby lowering connectivity between adjacent electrode material particles.

A significant consequence of this degradation is a drop in the capacity of the battery cell as it is charged and discharged. As used herein, capacity of a battery cell refers to the maximum current that a battery cell can supply over a given time period and is commonly expressed in ampere-hours (Ah). For example, if a battery cell is rated for 1000 mAh, then it should be capable of supplying 1000 mA over a one-hour period before it needs recharging. While capacity rating provides a basis for what type of battery can best meet the needs of a particular system, it only provides a measure of the battery's initial capabilities. Any decrease in capacity due to degradation of the battery cell during storage and/or use will compromise the battery's ability to deliver effectively store and deliver energy.

Given the chemical, mechanical and thermo-dynamic processes that occur within the battery cell and contribute to the degradation, the battery cell can be monitored to provide real-time information. For example, metrics of interest for real-time monitoring include amount of degradation in battery capacity as well as, but not limited to, amount of remaining charge in a battery and remaining useful battery life. Knowledge of the internal state of the battery cell can help determine charging times, appropriate discharge strategies, balancing between different cells in a battery pack, and/or thermal management within a battery pack.

The current capacity of a battery cell over the as-manufactured or initial capability can be used to define one metric for a battery cell's state of health. The state of health metric reflects the degradation of the battery and/or the battery pack and can be based on a decrease in the available capacity that a battery can deliver or an increase in the internal resistance thereof. The state of health metric can be determined using data obtained by measuring the voltage and current during the charge and discharge stages and estimating, for example, the decay in capacity and state of health based on current, voltage, and temperature measurements. In general, a 20% decrease in deliverable capacity can represent a threshold beyond which the battery performance begins to deteriorate rapidly. While a decrease in the deliverable capacity or an increase in internal resistance may reflect degradation in a lithium-ion battery system, this only relates to reduced performance and does not address safety. Gas generation and changes to the structure of the cell also capture performance-related information as well as information related to unsafe conditions that could be exacerbated as the battery cell is further stressed. Thus, investigation of the internal cell structure can help provide a more complete state of health evaluation that includes decreases in both performance and safety.

Battery Health Monitoring Device

Embodiments of the disclosed subject matter can use ultrasonic assessment of the internal structure of an energy storage device, for example, a battery cell, in order to provide information regarding a state of health of the assessed battery cell. Such information can be used alone or in conjunction with other state of health metrics to provide a more complete picture of the state of health of a battery cell or a battery pack including multiple battery cells.

Ultrasonic assessment detects changes in acoustic impedance, such as an interface between two materials, through measurement of reflected and/or transmitted acoustic signals. Modes of assessment can include a pulse-echo mode, a through-transmission mode, or both. In the pulse-echo mode, a sensor is arranged to detect ultrasound reflected from the interior of the battery cell. In the through-transmission mode, a sensor is arranged to detect ultrasound transmitted through the interior of the battery cell (e.g., by being located opposite the ultrasonic source or on a side of the battery cell opposite the ultrasonic source). In either mode, the source and sensor are configured to generate and detect, respectively, sound having a frequency in the ultrasound range, for example, greater than 1 MHz.

These assessment modes can be used to assess, among other things, swelling, electrode expansion, electrode delamination, voiding, and/or electrode ruffling within an assessed battery cell. These degradation mechanisms may be related to degradation resulting from, for example, typical charge/discharge cycling, intermittent operation at an elevated temperature that may be within or above specified operating limits, or mechanical and thermomechanical stresses acting on the cell during its operation. Based on the detected ultrasound, a metric can be provided for the degradation within the battery cell. For example, the amplitude of the reflected pulse and/or transmitted pulse can be used as a metric to assign a degradation level to the electrodes within the battery. Alternatively or additionally, a controller can make a determination about the state of health of the battery cell based on the detected ultrasound alone or along with other information regarding operating characteristics of the battery cell.

The ultrasonic source (e.g., a pulser or transducer) can emit pulses of ultrasonic energy at a specific frequency. Selection of the appropriate ultrasonic source and the corresponding assessment frequency can be based on the battery cell to be investigated, including among other things, the thickness of the battery cell, the geometry of the battery cell, and the temperature of assessment. Generally, a lower frequency transducer can be used to penetration into thick, more attenuating, and/or highly scattering battery cell materials, and a higher frequency transducer can be used for thinner, lower attenuating, and/or lower scattering battery cell materials. The ultrasonic source can be provided adjacent to an external surface of the battery cell and arranged to direct the ultrasonic energy into the interior of the battery cell. For example, an emission direction of the ultrasonic energy may be perpendicular to the plane of one or more electrode layers within the interior of the battery cell.

The ultrasonic sensor (e.g., a transducer) can detect ultrasonic energy in a broad range of ultrasound frequencies or limited to the specific frequency emitted by the ultrasonic source. As with the ultrasonic source, the ultrasonic sensor can be provided adjacent to an external surface of the battery cell and arranged to detect ultrasonic energy coming from the interior of the battery cell, e.g., reflected or transmitted ultrasound. In some embodiments, the ultrasonic source and the ultrasonic sensor can be parts of a single transducer, for example, for use in a pulse-echo mode configuration. In other embodiments, the source and sensor can be separate components disposed at different portions on the battery cell.

The ultrasonic source and/or the ultrasonic sensor can be disposed on the battery cell through a respective couplant. For example, the couplant may be disposed between and in contact with an external surface of the battery cell and a corresponding active surface of the ultrasonic source and/or the ultrasonic sensor. Thus, ultrasound traveling to or from the battery cell would pass through the couplant. The couplant provides a pathway to/from the battery cell for the ultrasound in order to avoid attenuation due to exposure of the ultrasound to air or other high attenuation mediums, which may otherwise compromise assessment of the battery cell. The couplant may be a separate component, for example, an encapsulated gel or gel pad, that is placed between the battery cell and the source or sensor, or attached to the source, sensor, or battery cell surface. Alternatively, the couplant may be integrated with the source or the sensor, e.g., as the material of an emission or detection face thereof.

Appropriate couplants can be selected based on acoustic velocity, impedance, and attenuation, as well as other factors, for example, as discussed in "Approximate Material Properties in Isotropic Materials," published in *IEEE Transactions on Sonics and Ultrasonics,* May 1985, SU-32(3): pp. 381-94, which is hereby incorporated by reference herein. In some embodiments, the couplant is a hydrocarbon grease. In other embodiments, the couplant is a pad of encapsulated gel. For example, the gel pad includes one or more polymers having an attenuation with respect to the applied ultrasonic frequencies similar to or approaching that of water. The gel can be a dry couplant elastomer comprising a blend of isomers of branched homopolymers with an attenuation of 5 dB relative to water, for example, as described in "Ultrasonic Properties of a New Low Attenuation Dry Couplant Elastomer," by Ginzel et al., April 1994, which is also incorporated by reference herein in its entirety. Other examples of couplants include but are not limited to the Water Gel Ultrasound Solid Gel Pad by BlueMTech (BlueMTech, Korea) and the AquaFlex® Ultrasound Gel Pad (Parker Laboratories, USA). Other couplants can also be used according to one or more contemplated embodiments.

The detected ultrasound from the battery cell may be evaluated as either an A-scan or C-scan. In general, A-scans can provide a determination of the state of health of the battery cell, and C-scan can be used to image an interior of the battery cell, for example, to visualize and locate regions of degradation. As used herein, A-scan refers to an amplitude modulation scan, i.e., the actual waveform of the acoustic signal obtained by the sensor. After application of an ultrasonic pulse to the battery cell, the resulting detected signal can be graphed where the horizontal axis is time and the vertical axis is amplitude.

In contrast, C-scan refers to scanning the transducer in one or two dimensions, e.g., raster-scanning the source/sensor over the entire surface area of the battery cell to produce a digitized image. After application of an ultrasonic pulse at each scanned position, the resulting detected signal at a particular time (corresponding to a particular depth in the battery cell, for example, as determined by placement of the data gate) is graphed to provide a map of the interface at that depth. The data gate targets an interface of interest within the thickness of the sample through the assessment of a portion of the corresponding A-scan waveform. For example, the interface of interest can be defined by positioning a rectangular frame over the portion of the A-scan that corresponding with the interface of interest using appropriate image processing software. The larger the time value associated with the data gate on the time axis of the A-scan, the greater the depth of interface of interest within the battery cell. By moving the gate position in time on the A-scan, different depths within the sample can be imaged. If air, gas, or another medium is present at a particular interface, all of the ultrasonic signal from that particular region may be reflected back, which results in detectable areas on a C-scan. The presence of air or gas pockets due to inner delaminated regions or voids will also cause the shape of the A-scan waveforms, which are taken at different points over the interface of interest, to be different in the data-gate region. In cases of extreme delamination or separation between active material and corresponding current collector, a phase inversion of the A-scan signal occurs at the data-gate region.

Figure 3A:
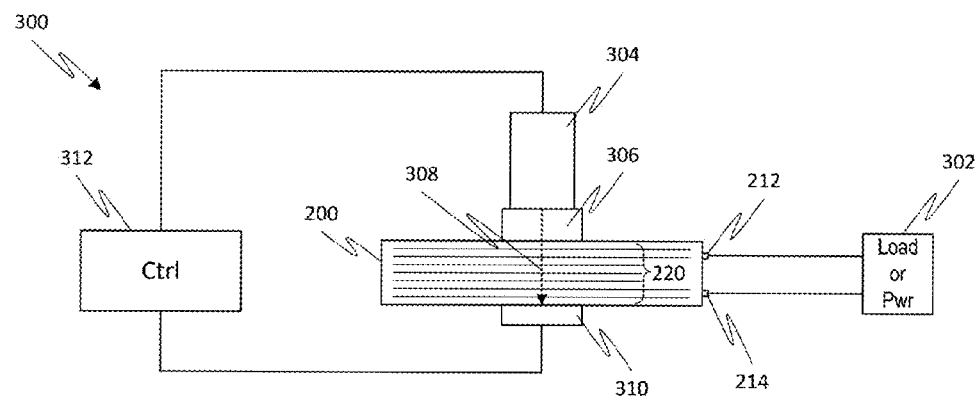
FIG. 3A is a simplified diagram of a battery health monitoring device in a transmitted ultrasound configuration, according to one or more embodiments of the disclosed subject matter.
Figure 3B:
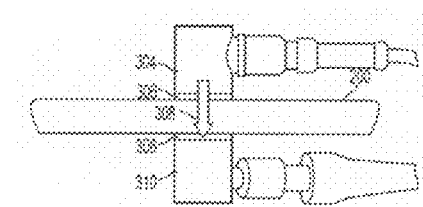
FIG. 3B shows a battery health monitoring device in a hand-held transmitted ultrasound configuration, according to one or more embodiments of the disclosed subject matter.

In one or more embodiments, a battery health monitoring device uses transmitted ultrasound to assess the internal volume of a battery cell, as described above, to make a determination regarding the state of health of the battery. For example, the battery health monitoring device 300 can be configured in a through-transmission mode for interrogating battery cell 200, as shown in FIG. 3A and FIG. 3B. The battery cell 200 may be connected to a load or charger 302 via terminals 212, 214 such that the battery cell 200 may be assessed while the battery cell 200 is in use, for example, during discharging or charging.

An ultrasound source 304 is disposed on a first side of the battery cell 200 with a couplant 306 between the battery cell 200 and the source 304. For example, an ultrasonic pulse 308 from the source 304 may be directed substantially perpendicular to the plane of one or all electrode layers 220 within the interior of the battery cell. Alternatively or additionally, at least an emission face of the source 304 is arranged substantially parallel to an external surface of the battery cell 200 and/or the plane of one or all electrode layers 220 within the interior of the battery cell 200.

The ultrasound sensor 310 can be disposed on a second side of the battery cell 200 opposite to the first side and arranged to receive the ultrasonic pulse 308 transmitted through the interior volume of the battery cell 200. Although not shown, the sensor 310 may also be disposed with a couplant between the battery cell 200 and the sensor 310. The sensor 310 can be arranged directly opposite to the source 304 so as to receive ultrasound 308 traveling in a straight line through the thickness of the battery cell 200, i.e., from a first side of the battery cell 200 facing the source 304 to a second side of the battery cell 200 facing the sensor 310.

A controller 312 (i.e., control unit) can be provided to control operation of the ultrasound source 304 and the ultrasound sensor 310 and to determine a state of health of the battery cell 200 based on signals from the ultrasound sensor 310. For example, the controller 312 may command the ultrasound source 304 to apply an ultrasonic pulse to the battery cell 200. The ultrasound sensor 310 can generate a signal based on detected ultrasound and convey the signal to the controller 312, which may use the signal to compose an A-scan. The resulting A-scan can be evaluated based on timing and/or amplitude of the detected pulse, for example, to make a determination regarding state of health of the battery cell 200. Such evaluation can include, but is not limited to, a comparison of the resulting A-scan with a previously obtained A-scan, which may be an A-scan of the battery cell 200 that was taken when the battery cell was in an as-manufacture or as-delivered non-cycled state. The controller 312 can also be configured to control the battery cell 200, for example, to alter charging, discharging, or other operations of the battery cell based on its determined state of health.

The source 304 and the sensor 310 can be disposed to assess one portion of the interior of the battery cell 200, for example, where structures within the interior of the battery cell 200 may be especially susceptible to degradation. Alternatively or additionally, the source 304 (and couplant 306) and the sensor 310 can move along a length (i.e., from left to right in FIG. 3A) and/or a width (i.e., into or out of the page in FIG. 3A) of the battery cell 200 to assess different portions of the battery cell 200. For example, the source 304 and the sensor 310 can move in order to obtain a C-scan of the battery cell 200 in order to image a particular defect or degradation. Controller 312 may control the source 304 and/or the sensor 310, for example, through an appropriate displacement mechanism, to provide the desired movement.

Figure 4:
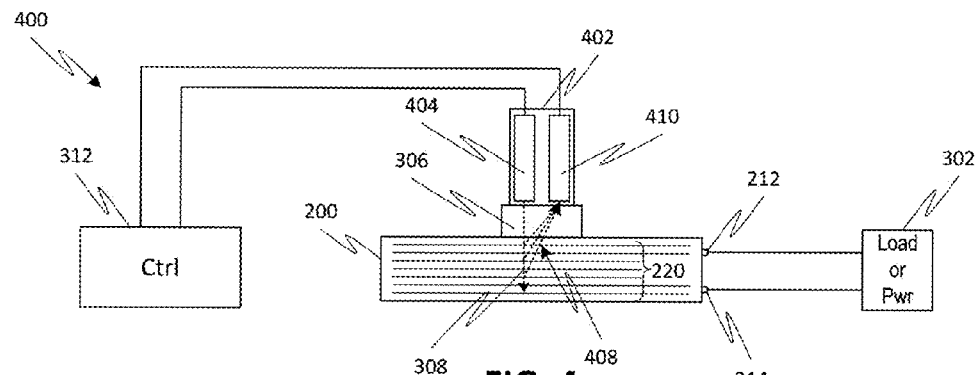
FIG. 4 is a simplified diagram of a battery health monitoring device in a reflected ultrasound configuration, according to one or more embodiments of the disclosed subject matter.

In one or more additional embodiments, a battery health monitoring device uses reflected ultrasound to assess the internal volume of a battery cell, as described above, to make a determination regarding the state of health of the battery. For example, the battery health monitoring device 400 can be configured in a pulse-echo mode for interrogating battery cell 200, as shown in FIG. 4. As with the previously described embodiment, the battery cell 200 may be connected to a load or charger 302 via terminals 212, 214 such that the battery cell 200 may be assessed while the battery cell 200 is in use, for example, during discharging or charging.

A transducer 402 is disposed on a first side of the battery cell 200 with a couplant 306 between the battery cell 200 and the transducer 402. The transducer 402 includes both an ultrasound source portion 404 and an ultrasound sensing portion 410. Although shown as separate portions, it is contemplated that the source portion 404 and the sensing portion 410 can be the same structure, for example, an active portion of the transducer 402 that serves an emitter when the ultrasound is emitted and then serves as a sensor after the ultrasound pulse is emitted.

For example, the ultrasound 308 (e.g., an ultrasonic pulse) from the source portion 404 may be directed substantially perpendicular to the plane of one or all electrode layers 220 within the interior of the battery cell. Alternatively or additionally, at least an emission/detection face of the transducer 402 is arranged substantially parallel to an external surface of the battery cell 200 and/or the plane of one or all electrode layers 220 within the interior of the battery cell 200. The sensing portion 310 receives ultrasound 408 reflected from structures (e.g., electrode layers 220) within the interior volume of the battery cell 200.

A controller 312 can be provided to control operation of the transducer 402 and to determine a state of health of the battery cell 200 based on signals from the transducer 402. For example, the controller 312 may command the transducer 402 to apply an ultrasound 308 to the battery cell 200. The transducer 402 can generate a signal based on detected ultrasound and convey the signal to the controller 312, which may use the signal to compose an A-scan. The resulting A-scan can be evaluated based on timing and/or amplitude of the detected energy, for example, to make a determination regarding state of health of the battery cell 200. Such evaluation can include, but is not limited to, a comparison of the resulting A-scan with a previously obtained A-scan, which may be an A-scan of the battery cell 200 that was taken when the battery cell was in an as-manufacture or as-delivered non-cycled state. The controller 312 can also be configured to control the battery cell 200, for example, to alter charging, discharging, or other operations of the battery cell based on its determined state of health.

The transducer 402 can be disposed to assess one portion of the interior of the battery cell 200, for example, where structures within the interior of the battery cell 200 may be especially susceptible to degradation. Alternatively or additionally, the transducer 402 (and couplant 306) can move along a length (i.e., from left to right in FIG. 4) and/or a width (i.e., into or out of the page in FIG. 4) of the battery cell 200 to assess different portions of the battery cell 200. For example, the transducer 402 can move in order to obtain a C-scan of the battery cell 200 in order to image a particular defect or degradation. Controller 312 may control the transducer 402, for example, through an appropriate displacement mechanism, to provide the desired movement. Alternatively or additionally, the transducer 402 may be fixed while the battery cell 200 is moved with respect to the transducer 402 to assess different portions of the battery cell 200. For example, the transducer can include a roller or wheel-shaped contact portion, such as but not limited to the Olympus Roller Ultrasonic Transducer (e.g., part number RT-0105-16SY by Olympus Corporation).

Figure 5:
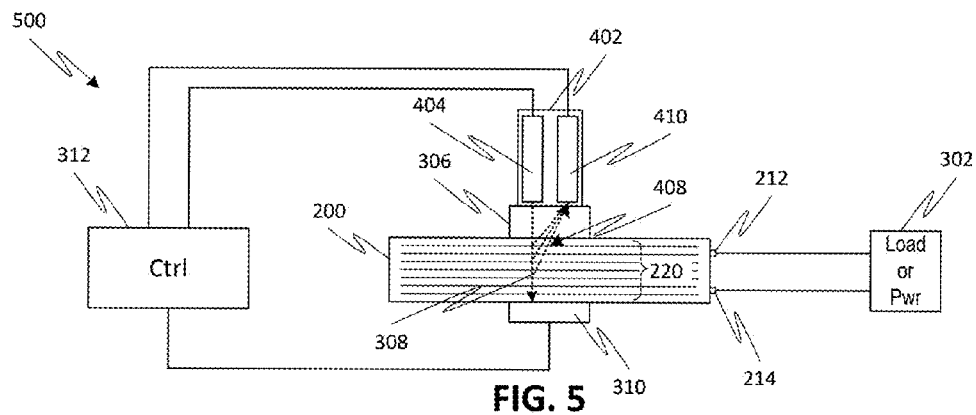
FIG. 5 is a simplified diagram of a battery health monitoring device in a transmitted and reflected ultrasound configuration, according to one or more embodiments of the disclosed subject matter.

In one or more additional embodiments, a battery health monitoring device can use transmitted and reflected ultrasound, either simultaneously or sequentially, to assess the internal volume of the battery cell to make a determination regarding the state of health of the battery cell. For example, the battery health monitoring device 500, as shown in FIG. 5, can combine the through-transmission assessment features of the embodiment of FIGS. 3A-3B and the pulse-echo assessment features of the embodiment of FIG. 4. As with the previously described embodiments, the battery cell 200 may be connected to a load or charger 302 via terminals 212, 214 such that the battery cell 200 may be assessed while the battery cell 200 is in use, for example, during discharging or charging. In addition, as with the previously described embodiments, the device 500 can be disposed to assess a single portion of the battery cell 200, or the device 500 and/or the battery cell 200 can be moveable to assess different portions of the battery cell 200, for example, to obtain a C-scan.

The controller 312 controls operation of the transducer 402 and sensor 310 and determines a state of health of the battery cell 200 based on signals from the transducer 402 and sensor 310. For example, the controller 312 may command the transducer 402 to apply an ultrasonic pulse 308 to the battery cell 200. Transducer 402 generates a signal based on detected, reflected ultrasound 408 and conveys a first signal to the controller 312, while sensor 310 generates a signal based on detected, transmitted ultrasound 308 and conveys a second signal to the controller 312. The controller 312 may use the first and second signals to determine a state of health of the battery cell, for example, by evaluating timing and/or amplitude in the detected signals and/or by comparison to previously obtained A-scans. For example, the controller 312 can use reflected ultrasound signals to localize degradation planes within the battery cell 200 while the transmitted ultrasound signals are used to measure the degree of degradation within the battery cell 200. The controller 312 can also be configured to control the battery cell 200, for example, to alter charging, discharging, or other operations of the battery cell based on its determined state of health.

Figure 6:
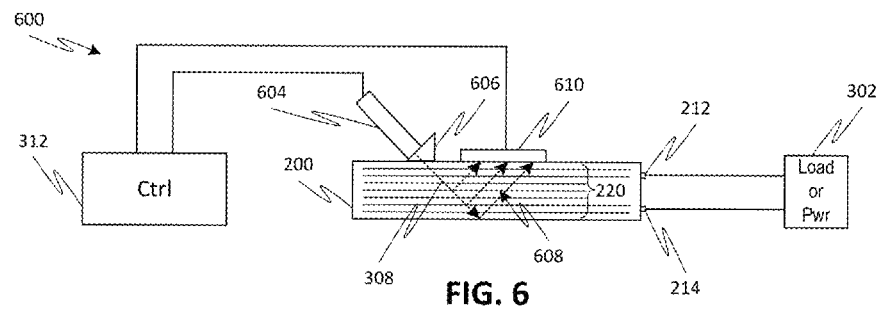
FIG. 6 is a simplified diagram of a battery health monitoring device in an offset reflected pulse configuration, according to one or more embodiments of the disclosed subject matter.

In one or more additional embodiments, a battery health monitoring device 600 uses reflected ultrasound to assess the internal volume of a battery cell 200, as shown in FIG. 6. Similar to the embodiment of FIG. 4, battery health monitoring device 600 is configured in a pulse-echo mode for interrogating battery cell 200. However, the ultrasound source 604 and the ultrasound sensor 610 are separate from each other and spaced on a first side of the battery cell 200. The ultrasound source 604 is disposed with an angled couplant 606 between the battery cell 200 and the source 604. The couplant 606 supports the source 604 in an angled configuration with respect to the surface of the battery cell 200 and/or the electrode layers 220 therein. Thus, the ultrasonic pulse 308 from the source 604 may be directed at an angle (i.e., not perpendicular or parallel) with respect to one or all electrode layers 220 within the interior of the battery cell. Alternatively or additionally, at least an emission face of the source 604 is arranged at angle with respect to an external surface of the battery cell 200 and/or the plane of one or all electrode layers 220 within the interior of the battery cell 200.

The ultrasound sensor 310 can be arranged to receive ultrasound 608 reflected from structures (e.g., electrode layers 220) within the interior volume of the battery cell 200.

The ultrasound sensor 310 can be arranged with an active face thereof parallel to an external surface of the battery cell 200 and/or the plane of one or all electrode layers 220 within the interior of the battery cell 200, as shown in FIG. 6. Alternatively, the ultrasound sensor 310 may have an angled configuration similar to that of ultrasound source 604, but shifted to be aligned with a direction of the reflected ultrasound 608.

As with the previously described embodiments, controller 312 can be provided to control operation of the source 604 and the sensor 610 and to determine a state of health of the battery cell 200 based on signals from the sensor 610. The battery cell 200 may be connected to a load or charger 302 via terminals 212, 214 such that the battery cell 200 may be assessed while the battery cell 200 is in use, for example, during discharging or charging.

The source 604 and the sensor 610 can be disposed to assess one portion of the interior of the battery cell 200, for example, where structures within the interior of the battery cell 200 may be especially susceptible to degradation. Alternatively or additionally, the source 604 (and couplant 606) and the sensor 610 can move along a length (i.e., from left to right in FIG. 6) and/or a width (i.e., into or out of the page in FIG. 6) of the battery cell 200 to assess different portions of the battery cell 200. For example, the source 604 and the sensor 610 can move in order to obtain a C-scan of the battery cell 200 in order to image a particular defect or degradation. Alternatively or additionally, the angle of the source 604 (or the angle of the sensor 610, when angled) can be varied to assess different portions of battery cell 200. Controller 312 may control the source 604 and/or the sensor 610, for example, through an appropriate angling and displacement mechanism, to provide these desired movements.

Figure 7:
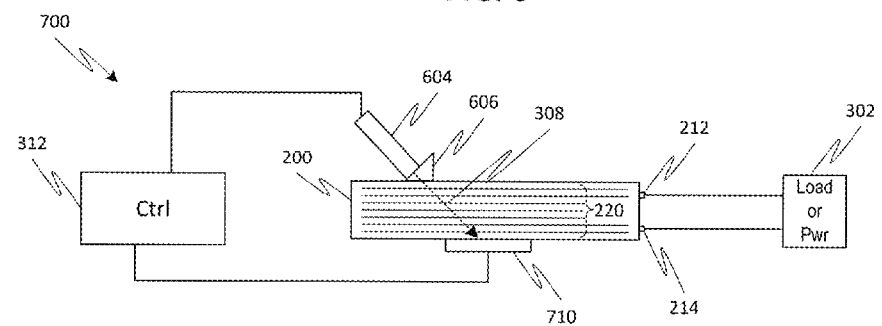
FIG. 7 is a simplified diagram of a battery health monitoring device in an offset transmitted ultrasound configuration, according to one or more embodiments of the disclosed subject matter.

In one or more additional embodiments, a battery health monitoring device 700 uses transmitted ultrasound to assess the internal volume of a battery cell 200, as shown in FIG. 7. Similar to the embodiment of FIG. 3A, battery health monitoring device 700 is configured in a through-transmission mode for interrogating battery cell 200. However, the ultrasound source 604 and the ultrasound sensor 710 are spaced from each other in a length direction of the battery cell. The ultrasound source 604 is disposed with an angled couplant 606 between the battery cell 200 and the source 604. The couplant 606 supports the source 604 in an angled configuration with respect to the surface of the battery cell 200 and/or the electrode layers 220 therein. Thus, the ultrasonic pulse 308 from the source 604 may be directed at an angle (i.e., not perpendicular or parallel) with respect to one or all electrode layers 220 within the interior of the battery cell. Alternatively or additionally, at least an emission face of the source 604 is arranged at angle with respect to an external surface of the battery cell 200 and/or the plane of one or all electrode layers 220 within the interior of the battery cell 200.

The ultrasound sensor 710 can be arranged to receive ultrasound 308 transmitted through the interior volume of the battery cell 200. The ultrasound sensor 710 can be arranged with an active face thereof parallel to an external surface of the battery cell 200 and/or the plane of one or all electrode layers 220 within the interior of the battery cell 200, as shown in FIG. 7. Alternatively, the ultrasound sensor 710 may have an angled configuration parallel to that of ultrasound source 604 so as to be aligned with a direction of the transmitted ultrasound 608.

As with the previously described embodiments, controller 312 can be provided to control operation of the source 604 and the sensor 710 and to determine a state of health of the battery cell 200 based on signals from the sensor 710. The battery cell 200 may be connected to a load or charger 302 via terminals 212, 214 such that the battery cell 200 may be assessed while the battery cell 200 is in use, for example, during discharging or charging.

The source 604 and the sensor 710 can be disposed to assess one portion of the interior of the battery cell 200, for example, where structures within the interior of the battery cell 200 may be especially susceptible to degradation. Alternatively or additionally, the source 604 (and couplant 606) and the sensor 710 can move along a length (i.e., from left to right in FIG. 7) and/or a width (i.e., into or out of the page in FIG. 7) of the battery cell 200 to assess different portions of the battery cell 200. For example, the source 604 and the sensor 710 can move in order to obtain a C-scan of the battery cell 200 in order to image a particular defect or degradation. Alternatively or additionally, the angle of the source 604 (or the angle of the sensor 710, when angled) can be varied to assess different portions of battery cell 200. Controller 312 may control the source 604 and/or the sensor 710, for example, through an appropriate angling and displacement mechanism, to provide these desired movements.

Figure 8:
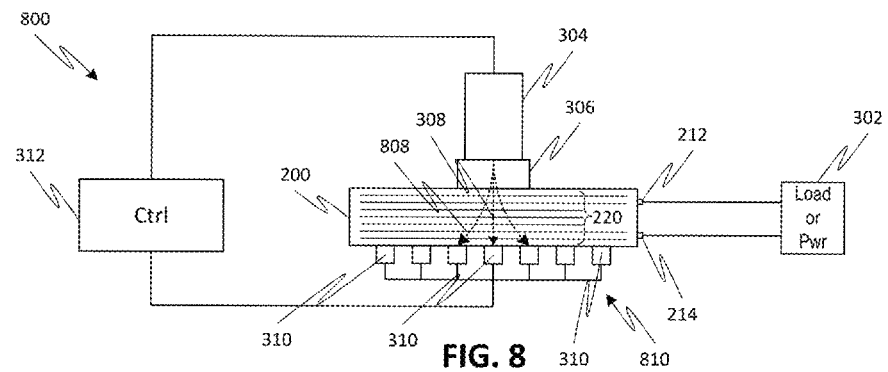
FIG. 8 is a simplified diagram of a battery health monitoring device with a single source and multiple sensors in a transmitted ultrasound configuration, according to one or more embodiments of the disclosed subject matter.

In one or more additional embodiments, a battery health monitoring device 800 uses transmitted ultrasound to assess the internal volume of a battery cell 200, as shown in FIG. 8. Similar to the embodiment of FIG. 3A, battery health monitoring device 800 is configured in a through-transmission mode for interrogating battery cell 200. However, an array 810 of ultrasound sensors 310 is provided on the opposite side of the battery cell 200 from the ultrasound source 304. For example, the ultrasonic pulse 308 from the source 304 may be directed substantially perpendicular to the plane of one or all electrode layers 220 within the interior of the battery cell. Alternatively or additionally, at least an emission face of the source 304 is arranged substantially parallel to an external surface of the battery cell 200 and/or the plane of one or all electrode layers 220 within the interior of the battery cell 200.

An ultrasound sensor 310 can be arranged to directly opposite the ultrasound source 304 so as to receive the ultrasound pulse 308 transmitted through the interior volume of the battery cell 200. The remaining ultrasound sensors 310 of the array 810 can be arranged to receive any spreading 808 of the ultrasound 308, for example, due to expansion of the ultrasound wave in the interior of the battery cell 200 and/or scattering or deflection by internal structures (e.g., electrode layers 220) of the battery cell. Each ultrasound sensor 310 can be arranged with an active face thereof parallel to an external surface of the battery cell 200 and/or the plane of one or all electrode layers 220 within the interior of the battery cell 200, as shown in FIG. 8.

As with the previously described embodiments, controller 312 can be provided to control operation of the source 304 and the sensors 310 and to determine a state of health of the battery cell 200 based on signals from the sensors 310. The battery cell 200 may be connected to a load or charger 302 via terminals 212, 214 such that the battery cell 200 may be assessed while the battery cell 200 is in use, for example, during discharging or charging.

The source 304 can be disposed to assess one portion of the interior of the battery cell 200, for example, where structures within the interior of the battery cell 200 may be especially susceptible to degradation. Alternatively or additionally, the source 304 (and couplant 306) and, optionally one or more of sensors 310 of the array, can move along a length (i.e., from left to right in FIG. 8) and/or a width (i.e., into or out of the page in FIG. 8) of the battery cell 200 to assess different portions of the battery cell 200. For example, the source 304 can move with respect to the sensor array 810, with different sensors 310 of the array serving as the sensor directly opposite the source 304 as the source 304 moves, in order to obtain a C-scan of the battery cell 200 and to image a particular defect or degradation. Controller 312 may control the source 304 and/or the sensor array 810, for example, through an appropriate displacement mechanism, to provide these desired movements.

Figure 9:
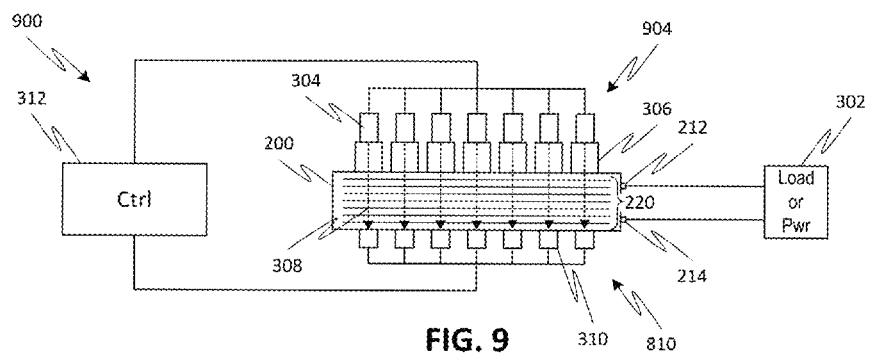
FIG. 9 is a simplified diagram of a battery health monitoring device with multiple sources and sensors in a transmitted ultrasound configuration, according to one or more embodiments of the disclosed subject matter.

In an alternative embodiment, multiple sources 304 can be provided as an array 904 similar to the array 810 of sensors 310, as illustrated in the battery health monitoring device 900 of FIG. 9. In such a configuration, each source 304 of the source array 904 may be arranged opposite to and correspond to a particular sensor 310 of the sensor array 810. To prevent cross-talk between adjacent sensors 310, each source 304 may be activated separately such that the corresponding through pulse 308 is detected by the corresponding sensor 310 before the next source 304 in the array is activated. Alternatively, sources 304 with sufficient spacing between each other may be activated at the same time, where the spacing minimizes the amount of cross-talk that may be detected by the corresponding sensors 310. For example, every other source 304 in array 810 may be actuated at the same time. In yet another alternative, sources 304 may be simultaneously activated and the sensors 310 of the array 810 simultaneously sampled and the resulting signals used in combination by the controller 312 to determine a state of health.

In still another alternative embodiment, multiple sources can be provided as a source array similar to that illustrated FIG. 9, but with multiple sensors corresponding to each source of the source array. Thus, the number of sensors in the sensor array may be more than the number of sources in the source array. For example, each source can have a primary sensor disposed directly opposite thereto and secondary sensors with the primary sensor therebetween, but the secondary sensors do not have a source disposed directly opposite thereto. Activation of each source may be sequential or simultaneous, for example, as described above with respect to FIG. 9.

Figure 10:
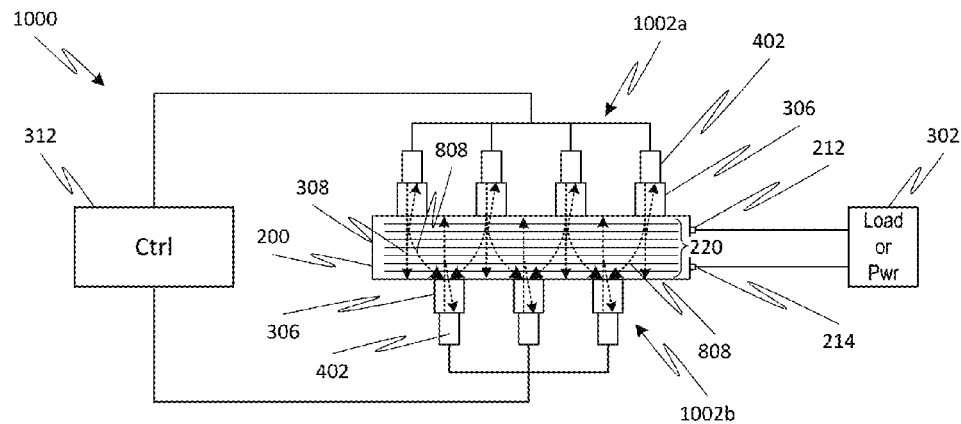
FIG. 10 is a simplified diagram of a battery health monitoring device with multiple transducers in a staggered arrangement, according to one or more embodiments of the disclosed subject matter.

In one or more additional embodiments, a battery health monitoring device 1000 uses reflected ultrasound to assess the internal volume of a battery cell 200, as shown in FIG. 10. Similar to the embodiment of FIG. 4, battery health monitoring device 1000 is configured in a pulse-echo mode for interrogating battery cell 200. However, a first array 1002a of ultrasound transducers 402 is provided on a first side of the battery cell 200, and optionally, a second array 1002b of transducers 402 can be provided on a second side opposite to the first side. Each transducer 402 may emit a pulse 308 into the interior of the battery cell 200 and can detect the resulting reflection from internal structures (e.g., electrode layers 220) within the battery cell 200.

To prevent cross-talk between adjacent transducers 402, each transducer 402 may be activated separately such that the corresponding reflected pulse 408 is detected by the same transducer 402 before the next transducer 402 in the array 1002a or 1002b is activated. Alternatively, transducers 402 with sufficient spacing between each other may be activated at the same time, where the spacing minimizes the amount of cross-talk that may be detected by the transducers 402. For example, every other transducer in each array 1002a, 1002b may be actuated at the same time. In yet another alternative, transducers 402 on one side of the battery cell 200 may be simultaneously activated. For example, the transducers 402 in array 1002a may be simultaneously activated and signals from transducers 402 in array 1002a simultaneously sampled.

In another example, transducers 402 in array 1002b can serve as through ultrasound sensors for the pulses emitted by transducers 402 in array 1002a. For example, each transducer 402 in array 1002b can receive any spreading 808 of the ultrasound 308, for example, due to expansion of the ultrasound wave in the interior of the battery cell 200 and/or scattering or deflection by internal structures (e.g., electrode layers 220) of the battery cell. Alternatively, each transducer 402 in array 1002b may be arranged directly opposite to a corresponding transducer 402 in array 1002a in order to receive transmitted pulse 308 directly. Thus, such a configuration may allow simultaneous pulse-echo and through-transmission detection with assessment from opposite sides of the battery cell.

As with the previously described embodiments, controller 312 can be provided to control operation of the source 304 and the sensors 310 and to determine a state of health of the battery cell 200 based on signals from the sensors 310. The battery cell 200 may be connected to a load or charger 302 via terminals 212, 214 such that the battery cell 200 may be assessed while the battery cell 200 is in use, for example, during discharging or charging.

Other configurations and arrangements of components of a battery health monitoring device beyond those specifically discussed above are also possible according to one or more contemplated embodiments. For example, the embodiment of FIG. 10 can be modified to include an array 1002a of transducers 402 only a single side of the battery cell 200. Other variations and combinations will be apparent to one of ordinary skill in the art, and embodiments of the disclosed subject matter are not limited to the specific embodiments illustrated in the drawings and described herein.

Although shown and described separately, it is contemplated that elements of the health monitoring device may be provided as one or more integral units. For example, the control unit can be integrated with the ultrasound source and/or the ultrasound sensor. In another example, the source, the sensor, and the control unit may comprise a single transducer with appropriate integrated circuitry for controlling operation of the source and sensor and processing the resulting signals. In yet another example, the control unit is separate from an integrated unit of the ultrasound source and the ultrasound sensor, and the control unit receives the signals from the integrated unit, for example, a hard-wired connection, over the Internet, or via a wireless connection. In still another example, the control unit comprises a separate module within a common housing of the source and the sensor. In any of the contemplated embodiments and examples, the health monitoring device can be provided as a handheld unit, for example, with individual manually positioned parts, as shown in FIG. 3B, or as an integrated unit that a user manually brings into contact with a particular battery cell.

EXAMPLES

Tests were performed on commercial lithium-ion batteries having a nominal voltage of 3.7 V. The electrodes were in a stacked configuration, and the separator was folded over in an accordion-like fashion so as to separate the stacked anode and cathode electrodes from each other. The anode and cathode materials were thus contained in alternating folds of the separator. Additionally, the anode and cathode materials were connected in series. Cell failure was defined as a drop in capacity of less than 80% (e.g., less than 75% or less than 72.5%) of the manufacturer-specified nominal capacity.

Figure 11:
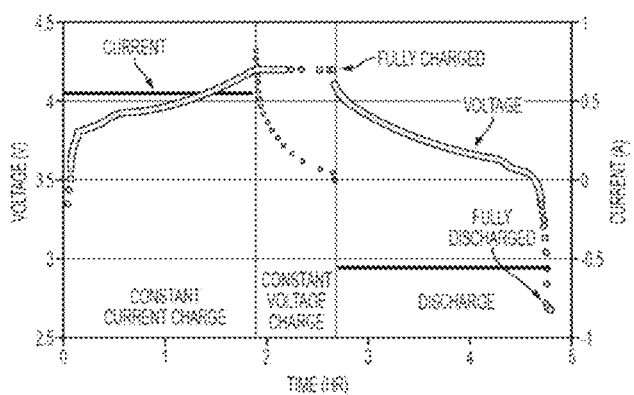
FIG. 11 is a graph illustrating an example of a profile for charging and discharging of a lithium ion battery.

Continuous battery charge/discharge cycling tests were performed using a commercial battery tester (e.g., a Cadex C8000) having four independent channels. The continuous cycling test was performed at a rate of 0.5 C. In addition to the cells that were charged and discharged at 0.5 C, a few uncycled, as-received cells were used as controls for periodic physical evaluation and comparisons. In accordance with the protocols described in UL 1642 and IEEE 1725, the batteries were cycled at room temperature to the specification of the manufacturer. Baseline capacity measurements were taken to ensure that full rated capacity was used during charging and discharging cycles. FIG. 11 shows an example of a constant current/constant voltage protocol that was used to charge and discharge the batteries. While the discharge mode occurred as a constant current load, actual operating conditions resulted in a variable current being applied to the battery.

Figure 12A:
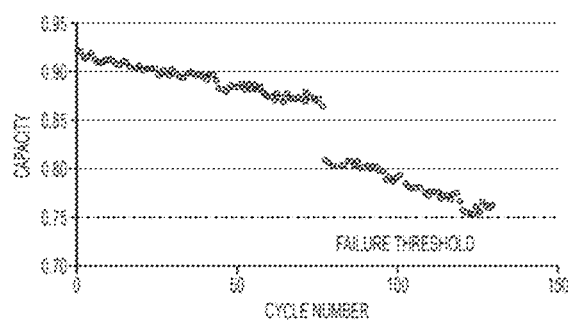
FIG. 12A is a graph illustrating changes in battery capacity versus cycles of charge and discharge for a tested lithium ion battery cell.
Figure 12B:
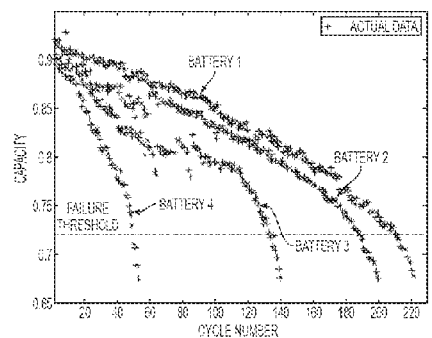
FIG. 12B is a graph illustrating examples of changes in battery capacity versus cycles of charge and discharge for various lithium ion battery cells.

In one example of a battery under test, a sharp drop in capacity was seen after the 76$^{th}$ cycle of the continuous charge/discharge cycling profile, as illustrated in FIG. 12A. There were no additional stresses placed on the cell, such as overcharging, overdischarging, or an increase in ambient temperature. Despite having this sudden drop in capacity during the 76$^{th}$ cycle, the cell did not reach the predefined failure threshold (e.g., 75% capacity) until after 133 cycles. A visual examination of the cell showed the cell had an increased external thickness as compared to the control battery cells. The change in thickness that was observed in the cycled cell was attributed to electrode ruffling and gas evolution within the cell. It is to be noted that the change in capacity illustrated in FIG. 12A is only an example, and other battery cells may have faster capacity loss rate (e.g., Battery 3, Battery 4) or slower capacity loss rate (e.g., Battery 1, Battery 2) until a predefined failure threshold (e.g., 72.5% capacity) is reached, as illustrated in FIG. 12B.

Ultrasonic assessment was performed on cycled and uncycled cells. The ultrasonic transducers were able to detect changes in acoustic impedance, such as at an interface between two materials, where a portion of the ultrasonic signal would be reflected back while the remainder would be transmitted through the interface and detected via through transmission. A portable digital ultrasonic sensor instrument was used to obtain A-scans of the acoustic signal. A hand-held assessment setup is shown in FIG. 3B. The cell was first disconnected from the Cadex C8000 battery tester and then connected to the ultrasonic detection setup. A 5 MHz, ¼-in. diameter ultrasonic pulser transducer was placed on top of the cell, and a 5 MHz, ¼-in. diameter ultrasonic receiver was placed on the bottom, as shown in FIG. 3B. A hydrocarbon-based grease was used as a couplant at the interfaces of the pulser and receiver with the outer casing of the cell. The through-transmission parameters are shown in Table 1 below.

TABLE 1

Examples of Parameters for Ultrasonic Assessment of Lithium Ion Battery Cell

| Parameter | Value |
| --- | --- |
| Ultrasound Source (e.g., Pulser) | 5 MHz, ¼-in diameter |
| Ultrasound Sensor (e.g., Receiver) | 5 MHz, ¼-in diameter |
| Ultrasound Frequency | 5 MHz |
| Energy | 400 V |
| Damping | 400 Ω |
| Receiver Filter | 1.5 MHz to 8.5 MHz |
| Gain | 50 dB |

Figure 13:
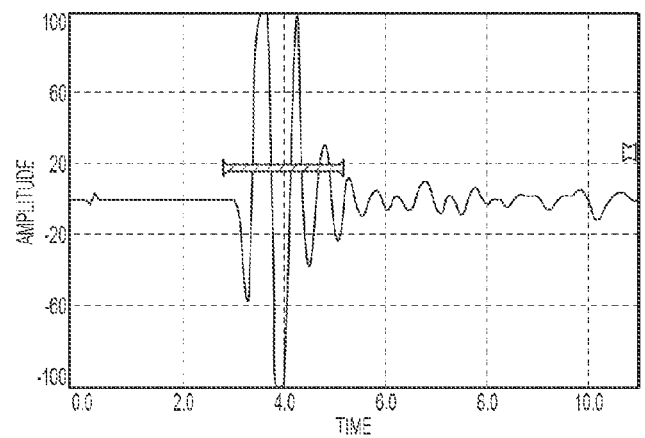
FIG. 13 is a graph of amplitude response detected by a battery health monitoring device for an ultrasonic pulse transmitted through a lithium ion battery cell in an as-manufactured state of health.
Figure 14:
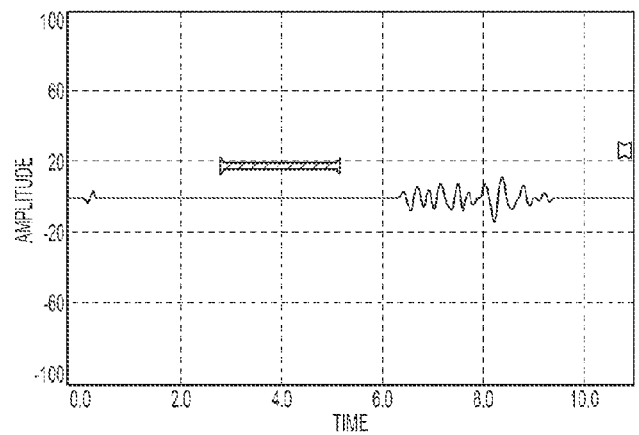
FIG. 14 is a graph of amplitude response detected by a battery health monitoring device for an ultrasonic pulse transmitted through a lithium ion battery cell in a compromised state of health.

After the cell was set up for through transmission, an A-scan representation was obtained on the display of the portable ultrasonic sensor. An A-scan from a non-cycled, as-manufactured control cell is shown in FIG. 13. As is apparent from FIG. 13, a strong through-pulse was detected by the receiver transducer, which pulse is consistent with the fact that the cell was uncycled and thus had not yet experienced any degradation. FIG. 14 shows an A-scan of the cycled cell that exhibited the drop in capacity after the 76$^{th}$ cycle. As is apparent from FIG. 14, the cycled cell transmitted only a very weak, delayed pulse. The weakening of the input ultrasonic pulse amplitude sensed by the receiver transducer suggests that the interfaces within the cell degraded due to at least one of electrode expansion, gas evolution, and residual stress developing along the interfaces as the cell is cycled. Thus, information from ultrasonic assessment of a cell can be used to evaluate the internal condition of structures of the cell and thereby provide a measure of the state of health of the cell.

Systems with Battery Health Monitoring

A battery-management system (BMS) can be incorporated into a host system that uses single cells or banks of cells arranged in series, parallel, or combinations thereof. A BMS enables safer and reliable operation by performing, among other things, state monitoring, charge control, and cell balancing (in multi-cell pack systems). Since certain battery operations (e.g., over-discharge) can reduce cell capacity, the BMS can monitor and control the battery cells based on safety circuitry incorporated within the battery pack to avoid such damaging operations. For example, whenever any abnormal conditions are detected, such as overvoltage or overheating, the BMS can notify the user and/or execute the predetermined corrective procedures.

The BMS can use one or more sensors to monitor battery conditions and can determine a state of health of individual batteries or the entire battery back responsive to signals from the sensors. Cells connected together in a battery pack may not be easily accessible once assembled. Thus, physical examination of individual cells for structural changes may require disassembly of the battery pack, which, in general, may not be safely performed by an end user. However, the disclosed ultrasonic health monitoring device provides information on the internal structural changes of a monitored battery cell. Thus, a BMS that incorporates information from the ultrasonic health monitoring device can improve overall safety and/or reliability of the battery pack. Early fault detection can help the BMS inform the user when to implement repair and maintenance strategies to prolong the life of the battery pack and/or avoid further degradation that could result in imminent or eventual battery failure.

As noted above, the battery cell being monitored can be a part of a larger battery pack that includes multiple battery cells connected in series, parallel, or any combination thereof. The ultrasonic transducers can be used to nondestructively and noninvasively monitor and assess the internal state of vital battery interfaces, e.g., the interface between the current collector and the corresponding anode and cathode materials. The ultrasonic data can be used to determine the instantaneous safety and health of the battery pack, for maintaining the battery system, and/or for evaluating the state of health over the course of the battery pack's lifetime.

Figure 15:
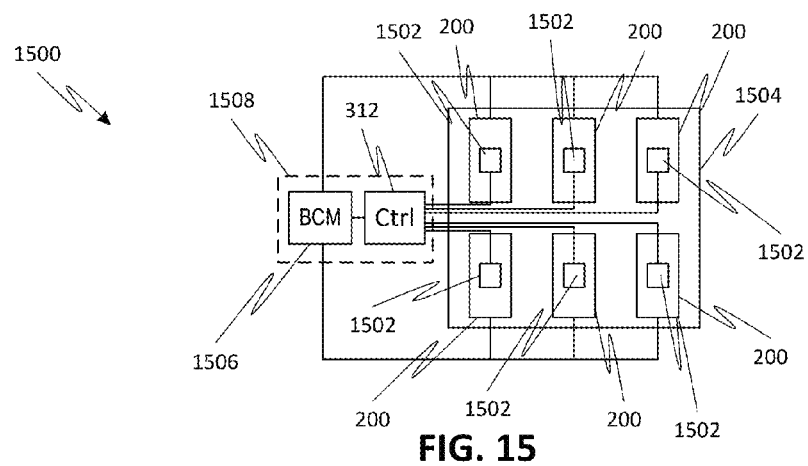
FIG. 15 is a simplified diagram of a battery system having multiple battery cells with a battery health monitoring device for each battery cell, according to one or more embodiments of the disclosed subject matter.

In one or more embodiments, a battery system employs a battery health monitoring device, for example, one or more of the battery health monitoring devices described above, to monitor individual battery cells within a battery pack. For example, the battery system 1500 can have a battery pack 1504 with a plurality of battery cells 200, each with a corresponding ultrasonic health monitoring device 1502, as shown in FIG. 15. The battery pack 1504 can be connected to a load or charging device (not shown). The ultrasonic health monitoring devices 1502 can thus assess and monitor the individual battery cells 200 while the battery pack 1504 is in use (e.g., charging or discharging).

Signals from the respective ultrasonic health monitoring devices 1502 can be conveyed to controller 312, where a determination of the state of health of each battery cell 200 can be made, for example, as described above. The battery system 1500 can also include a battery control module 1506, which regulates operation of the individual battery cells 200 within the battery pack 1504. Controller 312 may communicate state of health determinations to the battery control module 1506 for use in controlling operation of the individual battery cells 200. For example, battery control module 1506 may control charging and/or discharging profiles of each cell 200 and/or shut-down particular cells 200 in response to safety or reliability concerns. Together with controller 312, battery control module 1506 may form a battery management system (BMS) 1508, which may receive additional information regarding the battery cells 200 in determining appropriate operation or a state of health of the battery pack 1504. For example, in response to signals from the ultrasonic health monitoring devices 1502 indicative of the states of health for the various battery cells, the BMS 1508 can control charging/discharging within the battery pack 1504 to avoid defective or degraded cells 200, can determine an overall state of health of the battery pack 1504 or remaining useful lifetime for the battery pack 1504, and/or can provide an external alert regarding a degraded or dangerous condition of one of the battery cells 200 or the battery pack 1504.

Additionally, the BMS 1508 can receive signals from other sensors (not shown) that monitor one or more performance characteristics of the battery cells 200 and/or the battery pack 1504 in determining the state of health of the cells and/or the battery pack. For example, the performance sensors can be configured to measure battery cell internal resistance, battery cell discharge profile, battery cell charging time, battery cell current or voltage, battery cell temperature, battery cell strain, battery cell dimensions, or gas venting from the battery cell and to generate a measurement signal responsively thereto. Using the information from the performance sensors in combination with the information from the ultrasonic health monitoring devices 1502 can provide a more complete picture of the state of health of each individual battery cell 200 and the battery pack 1504 overall. Alternatively or additionally, health monitoring can be accomplished by monitoring confidence values computed by applying statistical pattern recognition techniques to the transient behavior of battery cells, transient responses, and correlation of the responses with models and validated with experimental data.

As with the ultrasonic health monitoring devices, performance sensors may be provided for each device. Alternatively, one or only some of the battery cells 200 are provided with performance sensors. For example, the performance sensors may be provided to one or more battery cells 200 within the pack 1504 that are more susceptible to degradation. Alternatively or additionally, one or more of the performance sensors may be shared among multiple battery cells 200. For example, a single temperature sensor may be provided for the entire battery pack 1504 or a subset of battery cells 200 within the battery pack 1504 and can measure a temperature that is associated with each of the battery cells 200.

Figure 16:
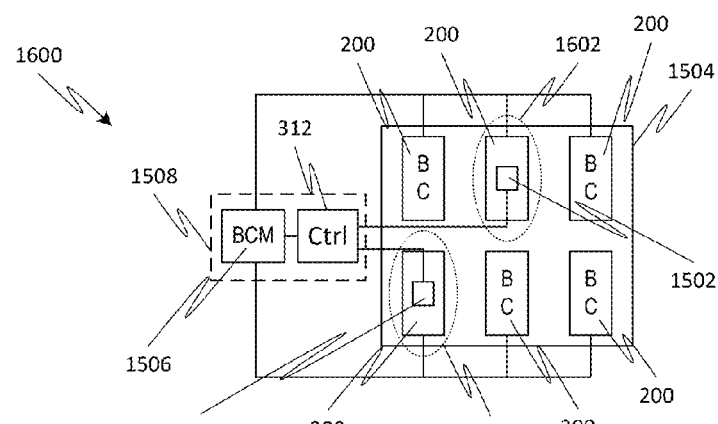
FIG. 16 is a simplified diagram of a battery system having multiple battery cells with a battery health monitoring device for only some of the battery cells, according to one or more embodiments of the disclosed subject matter.

In yet another alternative, one or only some of the battery cells 200 can be provided with ultrasonic health monitoring devices, for example, as with battery system 1600 in FIG. 16. In contrast to the embodiment of FIG. 15, only the subset 1602 of the plurality of battery cells 200 are provided with an ultrasonic health monitoring device 1502. The number of battery cells 200 within subset 1602 that receive an ultrasonic health monitoring device may be limited, for example, to no more than one-third of the total battery cells 200 within pack 1504, and may be even further limited to less than 10%.

The controller 312 can use information from the ultrasonic health monitoring devices 1502 associated with the subset 1602 to infer or predict the state of health of the remaining cells 200 within the battery pack 200. For example, the ultrasonic health monitoring devices may be provided to one or more battery cells 200 within the pack 1504 that are more susceptible to degradation. In such an example, presumably the degradation of battery cells 200 outside the subset 1602 would be less than the degradation of battery cells 200 within the subset 1602, such that information from the ultrasonic health monitoring devices 1502 represents a worst-case scenario for the battery pack 1504.

Figure 17:
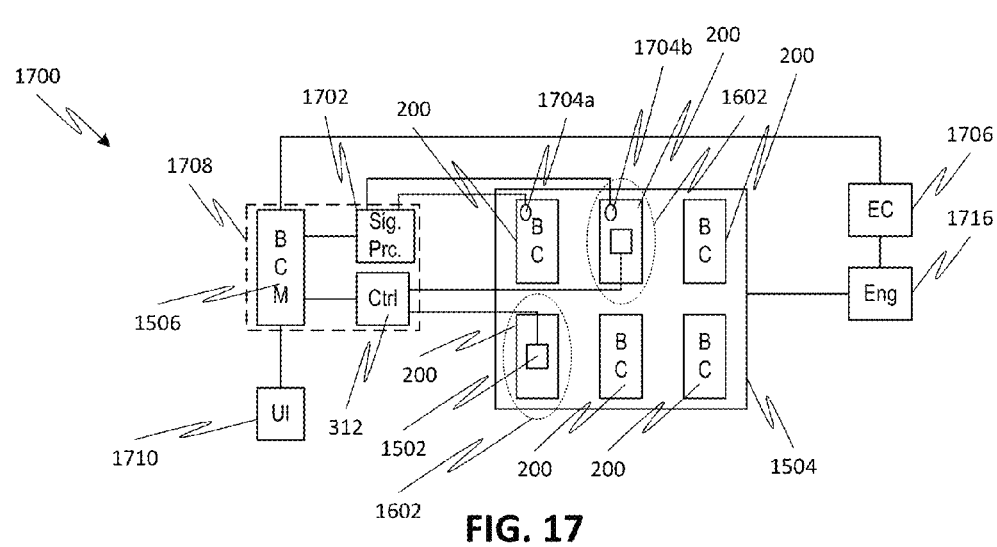
FIG. 17 is a simplified diagram of an automotive battery system employing battery health monitoring devices, according to one or more embodiments of the disclosed subject matter.

In one or more embodiments, a battery system with in-situ ultrasonic health monitoring is provided in an automotive application, for example, as an energy source for a hybrid-electric or all electric vehicle. For example, an automobile system 1700 can have a battery pack 1504 with a plurality of battery cells 200, as shown in FIG. 17. The battery pack 1504 can be connected to an electric motor 1716, which drives wheels of the vehicle. An engine controller 1706 monitors and regulates performance of the electric motor 1716, for example, in response to drive conditions or user input.

Ultrasonic health monitoring devices 1502 are provided to a subset 1602 of the battery cells 200 for interrogating and monitoring a state of health of the cells 200 and the battery pack 1504, as described above. In addition, performance sensors 1704 are provided to some of the battery cells 200 for interrogating and monitoring performance characteristics of the battery cells 200. A performance sensor signal processor 1702 receives signals from the performance sensors and conveys information regarding the performance characteristics to the battery control module 1506 responsively thereto. For example, the performance sensors can be configured to measure at least one of battery cell discharge profile, battery cell charging time, battery cell current or voltage, and battery cell temperature and to generate a measurement signal responsively thereto.

One or more performance sensors may be associated with a same battery cell 200 as one of the ultrasonic health monitoring devices 1502, for example, performance sensor 1704b monitoring battery cell 200 in subset 1602. Alternatively or additionally, one or more performance sensors may be associated only with a battery cell 200 that is not monitored by one of the ultrasonic health monitoring devices 1502, for example, performance sensor 1704a.

Selection of the subset 1602 of cells 200 that are to receive an ultrasonic health monitoring device and/or a performance sensor may be based on, for example, susceptibility to degradation or exposure to degrading conditions. The most vulnerable cells in the battery pack may be a result of the particular arrangement of the cell 200 in the battery pack 1504, for example, cells 200 that are arranged closer to an engine 1716 or that may see higher temperatures than other cells 200 in the pack 1504. The subset 1602 of sampled cells 200 can be used to predict a state of health of entire battery pack 1504, or can be used to provide a fault indication if one of the monitored cells in the subset 1602 catastrophically fails or is in danger of imminent failure. For example, sampling may be such that less than 5% of cells 200 are monitored. In an example, the number of battery cells 200 in battery pack 1504 is three-hundred and only between five and ten, inclusive, of the total number of battery cells 200 in the pack 1504 are monitored.

The output signals from the ultrasonic health monitoring devices 1502 can be integrated into the an automotive battery management system (aBMS) 1708, which can include, among other things, ultrasonic health monitoring controller 312, performance sensor signal processor 1702, and battery control module 1506. In the case of an automobile, by selective placement of such ultrasonic health monitoring devices 1502 on the battery cells 200 within the battery pack 1504, the onboard aBMS 1708 can provide indicators that show the state of the health, usage, performance, and longevity of the battery pack 1504.

Using the techniques described herein, the aBMS 1708 can provide real-time, in-situ monitoring of representative batteries (e.g., subset 1602) within the battery pack 1504. When an abnormal condition is detected, such as an electrode delamination beyond a set threshold or battery cell swelling due to overheating, the aBMS 1708 can notify onboard safety systems (e.g., via engine controller 1706 or other onboard controllers), execute a set of corrective procedures (e.g., via battery control module 1506), and/or notify a user, operator, manufacturer or other external entity (e.g., via user interface 1710). For example, the user interface 1710 may comprise an on-board dashboard indicator. Alternatively or additionally, the user interface 1710 is a communication device that allows transmission of data to an external computer or system, for example, a wireless connection to a user's smartphone or an Internet transmission to the automobile manufacturer. In addition to providing alarms due to adverse events, incorporation of this technique allows real-time recording of degradation within the representative battery cell 1502 of the battery pack 1504.

Figure 18:
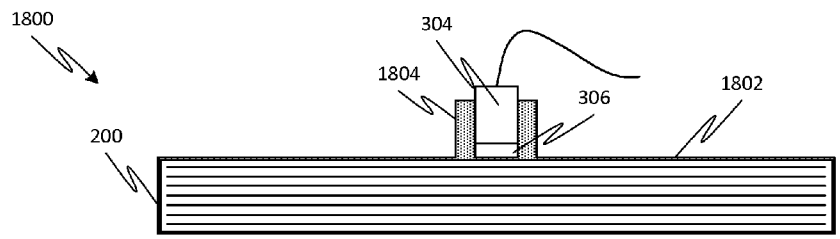
FIG. 18 is a simplified diagram illustrating mounting of an ultrasound component to a battery cell, according to one or more embodiments of the disclosed subject matter.

In one or more embodiments, the ultrasonic health monitoring device can be arranged on a surface of the battery cell 200 or battery pack 1504. For example, a battery configuration 1800 can have the ultrasonic health monitoring device mounted on an exterior surface 1802 of battery cell 200, as shown in FIG. 18. The exterior surface 1802 can include a mounting portion 1804 that retains the ultrasonic source 304 and the couplant 306 to the exterior surface 1802. A similar mounting portion may be provided for the sensor 310 (not shown), when necessary for a through-transmission configuration.

As noted above, the couplant 306 can comprise an encapsulated gel pad or insert. Such gel pads may enjoy a relatively long lifetime and may be reusable depending on the application. The couplant 306 can be pre-attached to or integral with the ultrasonic source 304 so that the combination of the source 304 and couplant 306 are inserted into the mounting portion 1804 at the same time. Alternatively, the couplant 306 may be a separate piece and inserted into the mounting portion 1804 before the source 304.

For example, the mounting portion 1804 may comprise a screw mechanism, locking mechanism, epoxy, glue, or any other retaining mechanism that can rigidly couple the ultrasonic health monitoring device to the surface. As the exterior surface 1802 moves, for example, due to swelling or other internal deformations, the mounting portion 1804 allows the ultrasonic health monitoring device to follow the movement of the exterior surface 1802.

Figure 19:
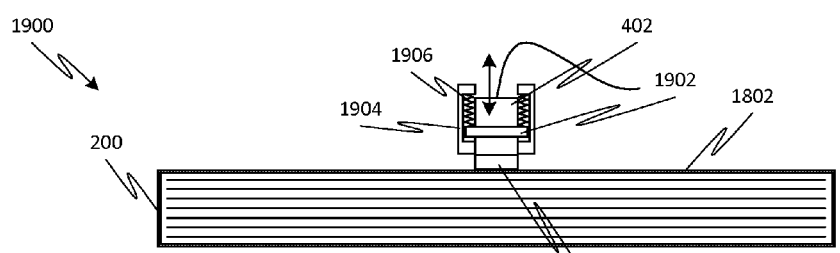
FIG. 19 is a simplified diagram illustrating flexible coupling of an ultrasound component to a battery cell, according to one or more embodiments of the disclosed subject matter.

Alternatively, the ultrasonic health monitoring device can be flexibly mounted so as to follow movement of the exterior surface 1802, as shown in the configuration 1900 of FIG. 19. For example, the ultrasonic source or transducer 402 can be provided with an annular lip 1902. A spring 1906 can provide an axially biasing force between lip 1902 and mounting support 1904 (e.g., a portion of the automotive body or other support structure independent of the particular battery cell 200) that urges the transducer 402 and couplant 306 into contact with the exterior surface 1802 of the battery cell 200. Movement of the exterior surface 1802 is accommodated by corresponding compression of spring 1906. Additionally, the movement of the transducer 402, which may be monitored by displacement sensors, for example, can provide an additional indicator of state of health of the battery cell 200, i.e., by providing a measure of the swelling of surface 1802. A similar configuration may be provided for the sensor 310 (not shown), when necessary for a through-transmission configuration.

Battery Health Testing Systems

Figure 20:
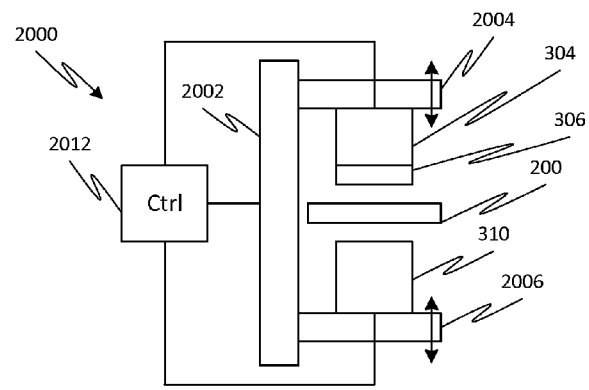
FIG. 20 is a simplified diagram of a generalized setup for interrogating a battery cell for determining a state of health thereof, according to one or more embodiments of the disclosed subject matter.

In one or more embodiments, a testing system employs a battery health monitoring device, for example, one or more of the battery health monitoring devices described above, to test individual battery cells, as part of a field return evaluation or quality control of a manufacturing process. For example, a battery testing system 2000 can have a testing platform 2002 with a first support 2004 for a first portion of an ultrasound health monitoring device and a second support 2006 for a second portion of the ultrasound health monitoring device, as shown in FIG. 20. For example, the first support 2004 may support the ultrasound source 304 and couplant 306 above the battery cell 200 and the second support 2006 may support the ultrasound sensor 310 below the battery cell 200, or vice versa.

In some configurations, only one of the first and second supports 2004, 2006 can be provided, for example, when only a pulse-echo mode is employed for testing the battery cells 200. Alternatively or additionally, an additional support (not shown) may be provided to hold battery cell 200 for assessment by the ultrasonic health monitoring device. One or more of the supports (when provided) may be configured to move in at least one dimension, for example, to bring the couplant 306 and ultrasound source 304 into contact with a first surface of the battery cell 200 and to bring the ultrasound sensor 310 into contact with a second surface of the battery cell 200. The couplant 306 can be, for example, a gel pad attached to an end of the ultrasonic source 304, which is brought into contact with each individual battery cell 200 conveyed to the testing platform 2002.

A controller 2012 can control the testing platform 2002 to move the support portions 2004, 2006 and/or battery cell 200 to perform ultrasonic assessment thereof. For example, the controller 2012 can control a conveying device (not shown) to move a battery cell 200 from a batch of cells to the testing platform 2002 for assessment. The controller 2012 can then control the testing platform 2002 to bring the couplant 306 and/or the sensor 310 into contact with the battery cell 200 and to subject the battery cell 200 to an ultrasonic pulse from the source 304. Alternatively or additionally, the source 304 and/or the sensor 310 may comprise a roller transducer, such as the Olympus Ultrasonic Roller Transducer referenced above. In such a configuration, the battery cell 200 may be linearly displaced between the rolling contact surfaces of the roller transducer to perform an assessment. Alternatively or additionally, the roller transducers can be displaced with respect to the battery cell 200 in order to perform an assessment.

The controller 2012 can receive a signal from sensor 310 indicative of the detected ultrasound and can provide an indication of the state of health, as described above. The controller 2012 can direct the battery cell 200 from the testing platform 2002 and/or provide an indication (e.g., a visual or auditory signal) based on a result of the assessment. Alternatively or additionally, the controller 2012 can move the ultrasonic health monitoring device and/or the battery cell 200 to allow assessment of more than one location within the interior of the battery cell 200, for example, by raster scanning across the surface of the battery cell 200.

In some embodiments, the battery cell 200 can be manually placed within the testing platform 2002 for evaluation. The controller can then control the testing platform 2002 to bring the couplant 306 into contact with the battery cell 200. In other embodiments, the testing platform 2002 can be actuated manually, for example, by a user moving one or more of the supports 2004, 2006 to contact the ultrasonic health monitoring device with the battery cell. Alternatively or additionally, the testing system 2000 can be configured as a handheld testing unit where a user can bring the testing platform 2002 into contact with the battery cell 200, for example, by inserting battery cell 200 into a receptacle of a handheld testing platform 2002.

In still other embodiments, the testing platform 2002 may have one or more of the supports 2004, 2006 that can passively move in response to a thickness of the battery cell 200 arranged between the supports 2004, 2006. For example, at least one of the supports 2004, 2006 can be spring mounted with a spacing between a surface of couplant 306 and a facing surface of the couplant (not shown) associated with sensor 310 being less than a thickness of the battery cell 200. Insertion of the battery cell 200 between the couplants biases the source 304 and sensor 306 against the respective surfaces of the battery cell 200.

Figure 21:
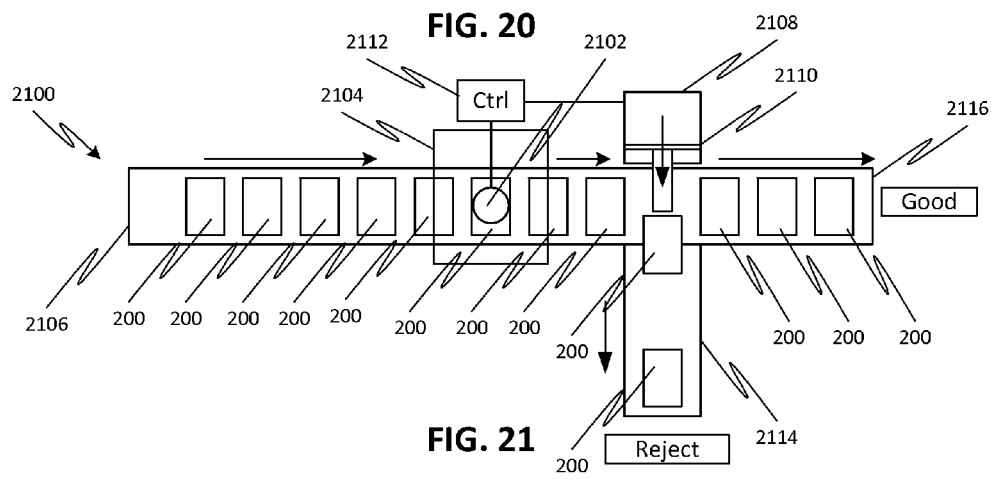
FIG. 21 is a simplified diagram of a setup for sequentially interrogating multiple battery cells for determining a state of health thereof, according to one or more embodiments of the disclosed subject matter.

In one or more embodiments, a testing system 2100 can optionally include a selection device that selects individual battery cells from a plurality of battery cells for respective assessment by the ultrasound source and sensor. For example, the selection device can include a conveying device 2106 that moves the battery cell 200 to a testing platform 2104, as shown in FIG. 21. For example, the conveying device 2106 can comprise a conveyor belt on which multiple battery cells 200 to be tested are disposed. As described above, the testing platform 2104 can ultrasonically test each individual battery cell 200 by bringing the ultrasonic health monitoring device 2102 into contact with the battery cell 200. The controller 2112 receives signals from the ultrasonic health monitoring device 2102 indicative of an internal condition of the assessed battery cell 200 and can control conveying device 2106 to direct the assessed battery cell 200 from the testing platform 2104 based thereon.

For example, battery cells 200 that do not meet predetermined criteria can be directed to a defect or reject bin while those that do meet the predetermined criteria can be directed to an acceptable bin for further processing. A redirection unit 2108 can have an arm 2110 that pushes a rejected battery cell 200 as it moves from the testing platform 2104 in order to move the rejected battery cell 200 via a different conveyor path 2114 to the reject bin. Acceptable battery cells 200 can continue along conveyor path 2116 to the acceptable bin. Other mechanisms for conveying the battery cells 200 to/from the testing platform 2104 and for redirecting the battery cells based on measured status are also possible according to one or more contemplated embodiments. For example, the conveying device can comprise a reel.

When the battery cell is a returned or reprocessed battery cell (i.e., one that has already undergone multiple charge/discharge cycles and/or has been stored for a significant period of time after manufacture), the controller (e.g., controller 2012 in FIG. 19 or controller 2112 in FIG. 20) may determine based on the detected ultrasound signal if the state of health of the battery cell 200 is sufficient for reuse (e.g., that the capacity of the battery cell has not degraded below 80%). Such state of health assessment can evaluate for degradation due to gas generation, active material delamination, electrode buckling, lithium ion diffusion, separator shrinkage, lithium plating, and tab shifting, for example. Those battery cells that are determined to be insufficient for reuse may be directed, for example, to a waste bin for proper disposal.

When the battery cell is a new battery cell (i.e., one that has not undergone multiple charge/discharge cycles and/or has been stored for a short period of time after manufacture), the controller (e.g., controller 2012 in FIG. 19 or controller 2112 in FIG. 20) may determine based on the detected ultrasound signal if the battery cell meets certain quality control criteria. Such quality control assessment can include determining the presence and location of metal particle inclusions, excessive current collector overhang, poor tab welds, agglomeration of active material, uneven thickness of active material, for example. Those battery cells that are determined to have quality control flaws may be directed, for example, to a defect bin for reprocessing.

Embodiments of the disclosed subject matter have been described above with respect to lithium-ion battery cells having a stacked electrode configuration and a substantially rectangular exterior shape. However, this discussion is merely intended to illustrate the principles and techniques of the disclosed systems, methods, and devices. The disclosed principles and techniques are also applicable to other battery cell configurations and other energy storage devices, and the above description should not be understood as limiting the present disclosure to lithium-ion batteries. For example, the energy storage device may have an interior volume comprised of a slurry without a well-defined electrode configuration. In another example, the energy storage device may have an exterior shape that is substantially spherical, oval, elliptical, or any other shape. In such configurations, the source and sensor may be disposed on the same surface, for example, at the same location (e.g., as part of the same transducer) or at different positions on the same surface (e.g., as separate transducers). Other structures and shapes are also possible according to one or more contemplated embodiments.

In addition, although embodiments have been described where each ultrasonic health monitoring device assesses a single battery cell, embodiments of the disclosed subject matter are not limited thereto. Rather, more than one battery cell can be disposed for assessment by a single ultrasonic health monitoring device. For example, in a through-transmission mode configuration, more than one battery cell can be stacked in a thickness direction thereof, with the ultrasound source disposed on a surface of the upper-most battery cell and the ultrasound sensor disposed on a surface of the lower-most battery cell. In another example, in pulse-echo mode configuration, more than one battery cell can be stacked in a thickness direction thereof, with a transducer disposed on an upper-most battery cell such that reflected ultrasound from battery cells in the stack can be received by the transducer. In still another example, in pulse-echo mode configuration, more than one battery cell can be stacked in a thickness direction thereof, with a first transducer disposed on a upper-most battery cell and a second transducer disposed on a lower-most battery cell so as to be able to assess the battery cell stack from both sides thereof.

Furthermore, although specific applications of the ultrasonic health monitoring device have been described with respect to battery management systems, automotive systems, battery field testing, and quality control assessment, embodiments of the disclosed subject matter are not limited thereto. Rather, the ultrasonic health monitoring device can employed in a wide array of applications beyond those specifically disclosed herein, such as, but not limited to, home or office back-up battery system monitoring, non-automotive electric vehicles (e.g., battery powered planes), battery warehouse inventory monitoring, etc.

In one or more first embodiments, a battery health monitoring device comprises an ultrasound source, a couplant, an ultrasound sensor, and a controller. The ultrasound source is configured to generate ultrasonic pulses having a frequency greater than 1 MHz. The couplant is arranged to convey the ultrasonic pulses from the ultrasound source to a monitored battery cell. The ultrasound sensor is configured to detect ultrasound having a frequency greater than 1 MHz and is arranged to detect ultrasound reflected from or transmitted through the monitored battery cell. The controller is configured to determine a state of health of the monitored battery cell based on a signal from the ultrasound sensor indicative of the detected ultrasound.

In the first embodiments or any other embodiment, the ultrasound source and the ultrasound sensor are part of a single transducer disposed on a same side of the monitored battery cell. The ultrasound sensor can be arranged to detect ultrasonic pulses reflected from an interior of the monitored battery cell.

In the first embodiments or any other embodiment, the ultrasound source is disposed on a first side of the monitored battery cell, and the ultrasound sensor is disposed on a second side of the monitored battery cell opposite from said first side. The ultrasound sensor can be arranged to detect ultrasonic pulses transmitted through an interior of the monitored battery cell.

In the first embodiments or any other embodiment, the battery health monitoring device further comprises a second ultrasound sensor configured to detect ultrasound having a frequency greater than 1 MHz. The second ultrasounds sensor is arranged to detect ultrasound reflected from or transmitted through the monitored battery cell. The second ultrasound source can be disposed on said first side of the monitored battery cell.

In the first embodiments or any other embodiment, the battery health monitoring device further comprises at least one additional ultrasound source, at least one additional couplant, and at least one additional ultrasound sensor. Each additional ultrasound source is configured to generate ultrasonic pulses having a frequency greater than 1 MHz. Each additional couplant corresponds to a respective additional ultrasound source and is arranged to convey the ultrasonic pulses from the respective additional ultrasound source to the monitored battery cell. Each additional ultrasound sensor is configured to detect ultrasound having a frequency greater than 1 MHz and is arranged to detect ultrasound reflected from or transmitted through the monitored battery cell. The controller is further configured to determine the state of health of the monitored battery cell based on signals from the ultrasound sensor and the at least one additional ultrasound sensor.

In the first embodiments or any other embodiment, the battery health monitoring device further comprises a plurality of additional ultrasound sensors. Each additional ultrasound sensor is configured to detect ultrasound having a frequency greater than 1 MHz and is arranged to detect ultrasound reflected from or transmitted through the monitored battery cell. The ultrasound sensor and the plurality of additional ultrasound sensors are arranged in an array on a same side of the monitored battery cell.

In the first embodiments or any other embodiment, the controller is configured to control the ultrasound source and the ultrasound sensor to perform an A-scan and to determine the state of health based on at least one of amplitude of the detected ultrasound and timing of the detected ultrasound.

In the first embodiments or any other embodiment, the couplant comprises hydrocarbon grease or an encapsulated gel.

In the first embodiments or any other embodiment, the battery health monitoring device further comprises a testing platform and a conveying device. The testing platform supports one or more of the ultrasound source, the couplant, and the ultrasound sensor. The conveying device moves individual battery cells from a plurality of battery cells to the testing platform for respective assessment by the ultrasound source and the ultrasound sensor.

In the first embodiments or any other embodiment, the controller is further configured to control the conveying device to direct assessed battery cells from the testing platform responsive to the determined state of health from the respective assessment.

In the first embodiments or any other embodiment, the battery health monitoring device further comprises a performance sensor. The performance sensor is configured to measure at least one of battery cell discharge profile, battery cell charging time, battery cell current or voltage, and battery cell temperature and to generate a measurement signal responsively thereto.

In the first embodiments or any other embodiment, the battery performance sensor is arranged to monitor a different battery cell from that monitored by the ultrasound sensor at a same time.

In the first embodiments or any other embodiment, the performance sensor and the ultrasound sensor monitor the same battery cell.

In the first embodiments or any other embodiment, the controller comprises a battery management system for a battery pack including a plurality of individual battery cells. The controller is further configured to determine a state of health of the battery pack based on the measurement signal from the performance sensor and the signal from the ultrasound sensor.

In the first embodiments or any other embodiment, the monitored battery cell comprises a lithium-ion battery cell with multiple electrode layers. The ultrasound source is arranged so as to direct the generated ultrasonic pulses perpendicular to a plane of one or more of the electrode layers.

In the first embodiments or any other embodiment, at least the ultrasound source and the couplant are mounted on a surface of the monitored battery cell.

In the first embodiments or any other embodiment, at least the ultrasound source and the couplant are coupled to a surface of the monitored battery cell so as to move with said surface.

In one or more second embodiments, a method of monitoring battery cell state of health comprises applying one or more ultrasonic pulses through a couplant to a first side of a lithium-ion battery cell, each ultrasonic pulse having frequency greater than 1 MHz. The method further comprises detecting ultrasound having a frequency greater than 1 MHz that is reflected from or transmitted through the lithium-ion battery cell using one or more ultrasound sensors coupled to the lithium-ion battery cell, and generating a signal indicative of the detected ultrasound.

In the second embodiments or any other embodiment, the method further comprises determining a state of health of the lithium-ion battery cell based at least in part on the generated signal indicative of the detected ultrasound.

In the second embodiments or any other embodiment, the determining a state of health is based on at least one of amplitude of the detected ultrasound and timing of the detected ultrasound.

In the second embodiments or any other embodiment, the lithium-ion battery cell is one of a plurality of cells in lithium-ion battery pack.

In the second embodiments or any other embodiment, the method comprises measuring at least one of battery cell discharge profile, battery cell charging time, battery cell current or voltage, and battery cell temperature of one of the lithium-ion battery cells. The method further comprises generating a measurement signal indicative of a result of said measuring, and determining a state of health of the lithium-ion battery pack based on the measurement signal and the signal indicative of the detected ultrasound.

In the second embodiments or any other embodiment, the lithium-ion battery cell has multiple electrode layers, and the applied one or more ultrasonic pulses are directed perpendicular to a plane of at least one of the electrode layers.

In the second embodiments or any other embodiment, at least one of the one or more ultrasound sensors is part of a transducer that generates said one or more ultrasonic pulses.

In the second embodiments or any other embodiment, the detecting ultrasound that is reflected from or transmitted through the lithium-ion battery cell comprises detecting one or more ultrasonic pulses reflected from an interior of the monitored battery cell.

In the second embodiments or any other embodiment, the detecting ultrasound that is reflected from or transmitted through the lithium-ion battery cell comprises detecting one or more ultrasonic pulses transmitted through an interior of the monitored battery cell.

In the second embodiments or any other embodiment, at least one of the one or more ultrasound sensors is positioned on the first side of the lithium-ion battery cell.

In the second embodiments or any other embodiment, at least one of the one or more ultrasound sensors is positioned on a side of the lithium-ion battery cell opposite from the first side.

In the second embodiments or any other embodiment, the applying one or more ultrasonic pulses and the detecting ultrasound are such that an A-scan is performed on the lithium-ion battery.

In the second embodiments or any other embodiment, the couplant comprises hydrocarbon grease or an encapsulated gel.

In the second embodiments or any other embodiment, the couplant comprises a gel pad.

In the second embodiments or any other embodiment, the method comprises attaching the couplant to an ultrasonic source configured to generate the one or more ultrasonic pulses. The method further comprises, prior to said applying, contacting the couplant to the first side of the lithium-ion battery cell and arranging the one or more ultrasound sensors to receive ultrasound reflected from or transmitted through the lithium-ion battery cell.

In the second embodiments or any other embodiment, the method comprises mounting the couplant and an ultrasonic source configured to generate the one or more ultrasonic pulses on an external surface of the lithium-ion battery cell. The mounting can be such that the couplant and the ultrasonic source move with the external surface of the lithium-ion battery cell.

In the second embodiments or any other embodiment, the method comprises, after the applying and detecting, repeating the applying and the detecting on a second lithium-ion battery cell and generating a second signal indicative of the detected ultrasound from the lithium-ion battery cell.

In the second embodiments or any other embodiment, the method comprises, before the repeating, at least one of: moving the second lithium-ion battery cell to a testing platform supporting an ultrasound source that generates the one or more ultrasonic pulses and the one or more ultrasound sensors, and moving the testing platform supporting the ultrasound source and the one or more ultrasound sensors to the second lithium-ion battery cell.

In the second embodiments or any other embodiment, the method comprises, after the repeating the applying and the detecting on the second lithium-ion battery cell, directing the second battery cell from the testing platform based on the second signal.

In the second embodiments or any other embodiment, the method comprises, at a same time as the applying one or more ultrasonic pulses and detecting ultrasound, at least one of charging the lithium-ion battery cell, discharging the lithium-ion battery cell, and repeatedly charging and discharging the lithium-ion battery cell.

In one or more third embodiments, a battery system with state of health monitoring comprises a battery pack, one or more ultrasonic health monitoring devices, and a battery management system. The battery pack comprises a plurality of individual lithium-ion battery cells. Each ultrasonic health monitoring device is arranged to assess one of the lithium-ion battery cells. Each ultrasonic health monitoring device comprises an ultrasound source that directs ultrasound at the respective lithium-ion battery cell. Each ultrasonic health monitoring device further comprises an ultrasound sensor that detects ultrasound reflected from or transmitted through the respective lithium-ion battery cell and generates a signal responsive thereto. The battery management system is configured to receive the signal from each ultrasound sensor and to determine a state of health of the battery pack based at least in part on said signal.

In the third embodiments or any other embodiment, each ultrasonic health monitoring device further comprises a couplant arranged between the ultrasound source and a surface of the respective lithium-ion battery cell.

In the third embodiments or any other embodiment, the couplant comprises a gel pad.

In the third embodiments or any other embodiment, each ultrasonic health monitoring device is mounted on a surface of the respective lithium-ion battery cell so as to move with said surface.

In the third embodiments or any other embodiment, each ultrasound source is configured to generated ultrasonic pulses having a frequency greater than 1 MHz, and each ultrasound sensor is configured to detect ultrasound having a frequency greater than 1 MHz.

In the third embodiments or any other embodiment, only some of the battery cells in the battery pack are provided with one of the ultrasonic health monitoring devices.

In the third embodiments or any other embodiment, up to 5% of the battery cells in the battery pack are provided with one of the ultrasonic health monitoring devices.

In the third embodiments or any other embodiment, each battery cell in the battery pack is provided with one of the ultrasonic health monitoring devices.

In the third embodiments or any other embodiment, the battery system further comprises one or more performance sensors. Each performance sensor is arranged to assess one or more of the lithium-ion battery cells. Each performance sensor is configured to measure battery cell internal resistance, battery cell discharge profile, battery cell charging time, battery cell current or voltage, battery cell temperature, battery cell strain, battery cell dimensions, or gas venting from the battery cell and to generate a measurement signal responsively thereto.

In the third embodiments or any other embodiment, the battery management system is configured to receive the measurement signal from each performance sensor and to determine the state of health of the battery pack based at least in part on said measurement signal.

In the third embodiments or any other embodiment, only a subset of the battery cells in the battery pack are provided with one of the ultrasonic health monitoring devices, and at least one performance sensors assesses one of the lithium-ion battery cells different from said subset.

In the third embodiments or any other embodiment, only a subset of the battery cells in the battery pack are provided with one of the ultrasonic health monitoring devices, and at least one performance sensors assesses one of the lithium-ion battery cells within said subset.

In the third embodiments or any other embodiment, the ultrasound source and the ultrasound sensor in each ultrasonic health monitoring device are part of a single transducer disposed on a same side of the respective lithium-ion battery cell.

In the third embodiments or any other embodiment, at least one ultrasound sensor is arranged to detect ultrasound reflected from an interior of the respective lithium-ion battery cell.

In the third embodiments or any other embodiment, at least one ultrasound sensor is arranged to detect ultrasound transmitted through an interior of the respective lithium-ion battery cell.

In the third embodiments or any other embodiment, the battery pack is constructed for use in an automotive vehicle.

In one or more fourth embodiments, a health monitoring device comprises an ultrasound source and an ultrasound sensor. The ultrasound source is configured to generate and direct ultrasound at an energy storage device. The ultrasound sensor is configured to detect ultrasound reflected from or transmitted through the energy storage device and to generate a signal responsive to the detected ultrasound from the energy storage device.

In the fourth embodiments or any other embodiment, the health monitoring device further comprises a couplant arranged between the ultrasound source and the energy storage device, and/or a couplant arranged between the energy storage device and the ultrasound sensor.

In the fourth embodiments or any other embodiment, the ultrasonic source comprises a couplant that contacts a surface of the energy storage device, and/or the ultrasonic sensor comprises a couplant that contacts a surface of the energy storage device.

In the fourth embodiments or any other embodiment, the couplant comprises hydrocarbon grease or an encapsulated gel.

In the fourth embodiments or any other embodiment, the ultrasound source and the ultrasound sensor are disposed on a same surface of the energy storage device and spaced from each other.

In the fourth embodiments or any other embodiment, the surface of the energy storage device is spherical, elliptical, oval, or rectangular.

In the fourth embodiments or any other embodiment, the ultrasound source and the ultrasound sensor are part of a single transducer, and the ultrasound sensor is arranged to detect ultrasound reflected from an interior of the energy storage device.

In the fourth embodiments or any other embodiment, the ultrasound source is disposed opposite to the ultrasound sensor with the energy storage device therebetween, and the ultrasound sensor is arranged to detect ultrasound transmitted through an interior of the energy storage device.

In the fourth embodiments or any other embodiment, a second ultrasound sensor is configured to detect ultrasound reflected from the energy storage device, and the ultrasound source and the second ultrasound sensor are part of a single transducer.

In the fourth embodiments or any other embodiment, the health monitoring device further comprises a plurality of additional ultrasound sensors. Each additional ultrasound sensor is configured to detect ultrasound reflected from or transmitted through the energy storage device, the ultrasound sensor. The plurality of additional ultrasound sensors are arranged in an array.

In the fourth embodiments or any other embodiment, the health monitoring device further comprises at least one additional ultrasound source and at least one additional ultrasound sensor. Each additional ultrasound source is configured to generate and direct ultrasound at the energy storage device. Each additional ultrasound sensor is configured to detect ultrasound reflected from or transmitted through the energy storage device and to generate a signal responsive to the detected ultrasound from the energy storage device.

In the fourth embodiments or any other embodiment, the health monitoring device further comprises a control unit configured to determine a state of health of the energy storage device based on signals from the ultrasound sensor and the at least one additional sensor.

In the fourth embodiments or any other embodiment, the health monitoring device further comprises a control unit that receives the signal from the ultrasound sensor. The control unit is configured to determine a state of health of the energy storage device responsive to said signal.

In the fourth embodiments or any other embodiment, the energy storage device comprises a battery cell and the control unit is configured to determine the state of health of the battery cell.

In the fourth embodiments or any other embodiment, the energy storage device comprises a lithium-ion battery cell and the control unit is configured to determine the state of health of the lithium-ion battery cell.

In the fourth embodiments or any other embodiment, the ultrasound source or the ultrasound sensor comprises the control unit.

In the fourth embodiments or any other embodiment, the ultrasound source and the ultrasound sensor are separate from the control unit.

In the fourth embodiments or any other embodiment, the energy storage device is a battery cell within a battery pack that includes a plurality of individual battery cells. The control unit comprises a battery management system for the battery pack, and the control unit is further configured to determine a state of health of the battery pack based on the signal from the ultrasound sensor.

In the fourth embodiments or any other embodiment, the control unit is configured to control the ultrasound source and the ultrasound sensor to perform an A-scan and to determine the state of health based on at least one of amplitude of the detected ultrasound and timing of the detected ultrasound.

In the fourth embodiments or any other embodiment, the generated and detected ultrasound comprises one or more ultrasonic pulses having a frequency greater than 1 MHz.

In the fourth embodiments or any other embodiment, the health monitoring device further comprises a testing platform and a selection device. The testing platform comprises the ultrasound source and the ultrasound sensor. The selection device selects individual energy storage devices from a plurality of energy storage devices for respective assessment by the ultrasound source and the ultrasound sensor of the testing platform.

In the fourth embodiments or any other embodiment, the selection device comprises a conveying system that moves the individual energy storage devices from the plurality of energy storage devices to the testing platform for the respective assessment.

In the fourth embodiments or any other embodiment, the conveying system comprises a conveyor belt or reel.

In the fourth embodiments or any other embodiment, the health monitoring device further comprises a control unit that receives the signal from the ultrasound sensor and determines a state of health of the energy storage device responsive to said signal. The control unit controls the conveying system to direct energy storage devices from the testing platform responsive to the determined state of health from the respective assessment.

In the fourth embodiments or any other embodiment, the health monitoring device is constructed as a handheld unit with the ultrasound source and the ultrasound sensor disposed therein.

In the fourth embodiments or any other embodiment, the energy storage device comprises a battery cell. The health monitoring device further comprises a second sensor configured to measure battery cell internal resistance, battery cell discharge profile, battery cell charging time, battery cell current or voltage, battery cell temperature, battery cell strain, battery cell dimensions, or gas venting from the battery cell and to generate a measurement signal responsively thereto.

In the fourth embodiments or any other embodiment, the energy storage device is one of a plurality of battery cells, and the second sensor is arranged to monitor a different battery cell from that monitored by the ultrasound sensor at a same time.

In the fourth embodiments or any other embodiment, the energy storage device is one of a plurality of battery cells, and the second sensor and the ultrasound sensor monitor the same battery cell.

In the fourth embodiments or any other embodiment, the energy storage device comprises a lithium-ion battery cell with multiple electrode layers, and the ultrasound source is arranged so as to direct the generated ultrasound perpendicular to a plane of one or more of the electrode layers.

In the fourth embodiments or any other embodiment, at least the ultrasound source is coupled to a surface of the energy storage device so as to move with said surface.

In one or more fifth embodiments, a method of monitoring an energy storage device comprises applying ultrasound to an energy storage device, detecting ultrasound reflected from or transmitted through the energy storage device, and generating a signal indicative of the detected ultrasound.

In the fifth embodiments or any other embodiment, the applying ultrasound to the energy storage device is via an ultrasonic source through a first couplant or the detecting ultrasound from the energy storage device is via an ultrasound sensor through a second couplant.

In the fifth embodiments or any other embodiment, the first couplant or the second couplant comprises hydrocarbon grease, an encapsulated gel, or a gel pad.

In the fifth embodiments or any other embodiment, the applying and detecting ultrasound comprises applying and detecting one or more ultrasonic pulses having a frequency greater than 1 MHz.

In the fifth embodiments or any other embodiment, the energy storage device comprises a battery cell, for example, a lithium-ion battery cell.

In the fifth embodiments or any other embodiment, the method further comprises determining a state of health of the energy storage device based at least in part on the generated signal indicative of the detected ultrasound.

In the fifth embodiments or any other embodiment, the determining a state of health is based on at least one of amplitude of the detected ultrasound and timing of the detected ultrasound.

In the fifth embodiments or any other embodiment, the energy storage device is a battery cell within a battery pack that includes a plurality of individual battery cells. The method further comprises measuring battery cell internal resistance, battery cell discharge profile, battery cell charging time, battery cell current or voltage, battery cell temperature, battery cell strain, battery cell dimensions, or gas venting of one of the battery cells. The method additionally comprises generating a measurement signal indicative of a result of said measuring, and determining a state of health of the battery pack based on the measurement signal and the signal indicative of the detected ultrasound.

In the fifth embodiments or any other embodiment, the measuring of one of the battery cells is of a different battery cell than the detecting ultrasound.

In the fifth embodiments or any other embodiment, the measuring of one of the battery cells is of a same battery cell as the detecting ultrasound.

In the fifth embodiments or any other embodiment, the energy storage device comprises a battery cell with multiple electrode layers, and the applying ultrasound comprises directing ultrasound perpendicular to a plane of at least one of the electrode layers.

In the fifth embodiments or any other embodiment, the detecting ultrasound that is reflected from or transmitted through the energy storage device comprises detecting ultrasound reflected from an interior of the energy storage device.

In the fifth embodiments or any other embodiment, the detecting ultrasound that is reflected from or transmitted through the energy storage device comprises detecting ultrasound transmitted through an interior of the energy storage device.

In the fifth embodiments or any other embodiment, the applying ultrasound and the detecting ultrasound are such that an A-scan is performed on the energy storage device.

In the fifth embodiments or any other embodiment, the applying and the detecting ultrasound comprises disposing an ultrasound source and an ultrasound sensor on a same surface of the energy storage device.

In the fifth embodiments or any other embodiment, the ultrasound source and sensor are part of a same transducer.

In the fifth embodiments or any other embodiment, the ultrasound source and sensor are spaced from each other on the same surface.

In the fifth embodiments or any other embodiment, the surface of the energy storage device is spherical, elliptical, oval, or rectangular.

In the fifth embodiments or any other embodiment, the applying and the detecting ultrasound comprises disposing an ultrasound source and an ultrasound sensor opposite from each other with the energy storage device therebetween.

In the fifth embodiments or any other embodiment, the method further comprises attaching a couplant to an ultrasonic source configured to generate ultrasound or to the energy storage device, and arranging one or more ultrasound sensors to receive ultrasound reflected from or transmitted through the energy storage device.

In the fifth embodiments or any other embodiment, the method further comprises mounting an ultrasonic source with an integral couplant on an external surface of the energy storage device. The ultrasonic source is configured to generate ultrasound. The mounting is such that the couplant and the ultrasonic source move with the external surface of the energy storage device.

In the fifth embodiments or any other embodiment, the method further comprises, after the applying and detecting, repeating the applying and the detecting on a second energy storage device and generating a second signal indicative of the detected ultrasound from the second energy storage device.

In the fifth embodiments or any other embodiment, the method further comprises, before the repeating, at least one of moving the second energy storage device to a testing platform supporting an ultrasound source that generates ultrasound and one or more ultrasound sensors, and moving the testing platform supporting the ultrasound source and the one or more ultrasound sensors to the second energy storage device.

In the fifth embodiments or any other embodiment, the method further comprises, after the repeating the applying and the detecting on the second energy storage device, directing the second energy storage device from the testing platform based on the second signal.

In the fifth embodiments or any other embodiment, the method further comprises, at a same time as the applying and the detecting ultrasound, at least one of charging the energy storage device, discharging the energy storage device, and repeatedly charging and discharging the energy storage device.

In the fifth embodiments or any other embodiment, the method further comprises measuring at least one of discharge profile of the energy storage device, charging time of the energy storage device, current or voltage of the energy storage device, temperature of the energy storage device, strain levels on the energy storage device, dimensions or change in dimensions of the energy storage, internal resistance of the energy storage device, and venting of gas from the energy storage device via a gas vent sensor or strain measurements.

In the fifth embodiments or any other embodiment, the energy storage device is a battery cell within a battery pack that includes a plurality of individual battery cells. The method further comprises determining a state of health of the battery pack based at least in part on the generated signal.

In the fifth embodiments or any other embodiment, the applying and the detecting ultrasound comprise supporting by hand an ultrasound source or an ultrasound sensor with respect to the energy storage device.

In the fifth embodiments or any other embodiment, the energy storage device comprises a battery cell with multiple electrode layers, and the applying ultrasound comprises directing generated ultrasound perpendicular to a plane of one or more electrode layers.

In any of the embodiments, a system can be configured to perform any method disclosed herein.

In any of the embodiments, a non-transitory computer-readable storage medium is embodied with a sequence of programmed instructions, and a computer processing system executes the sequence of programmed instructions embodied on the computer-readable storage medium to cause the computer processing system to perform any of the methods disclosed herein.

It will be appreciated that the modules, processes, systems, and devices described above, for example, the control unit, can be implemented in hardware, hardware programmed by software, software instruction stored on a non-transitory computer readable medium or a combination of the above. For example, a method for determining a state of health of one or more battery cells using ultrasonic assessment can be implemented, for example, using a processor configured to execute a sequence of programmed instructions stored on a non-transitory computer readable medium. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and devices, for example, the control unit, can be implemented as a single processor or as a distributed processor. Further, it should be appreciated that the steps mentioned herein may be performed on a single or distributed processor (single and/or multi-core). Also, the processes, modules, and submodules described in the various figures of and for embodiments herein, for example, the control unit, may be distributed across multiple computers or systems or may be co-located in a single processor or system. Structural embodiment alternatives suitable for implementing the modules, systems, or processes described herein, for example, the control unit, are provided below.

The modules, processes, systems, and devices described above, for example, the control unit, can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the methods, processes, modules, devices, and systems (or their sub-components or modules), for example, the control unit, may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or computer program products (software program stored on a non-transitory computer readable medium).

Furthermore, embodiments of the disclosed methods, processes, modules, devices, systems, and computer program product, for example, the control unit, may be readily implemented, fully or partially, in software using, for example, object or object-oriented software development environments that provide portable source code that can be used on a variety of computer platforms. Alternatively, embodiments of the disclosed methods, processes, modules, devices, systems, and computer program product, for example, the control unit, can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the methods, processes, modules, devices, systems, and computer program product, for example, the control unit, can be implemented in hardware and/or software using any known or later developed systems or structures, devices and/or software by those of ordinary skill in the art from the function description provided herein and with knowledge of battery assessment or health monitoring systems and/or computer programming arts.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for monitoring a state of health of an energy storage device, such as a lithium-ion battery cell. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A health monitoring device comprising:
   an ultrasound source configured to generate and direct ultrasound at an energy storage device;
   an ultrasound sensor configured to detect ultrasound reflected from or transmitted through the energy storage device and to generate a signal responsive to the detected ultrasound from the energy storage device; and
   a control unit that receives the signal from the ultrasound sensor, the control unit being configured to determine a state of health of the energy storage device responsive to said signal,
   wherein the control unit is configured to control the ultrasound source and the ultrasound sensor to perform an A-scan and to determine the state of health based on amplitude of the detected ultrasound and timing of the detected ultrasound, and
   wherein the energy storage device is a battery cell within a battery pack that includes a plurality of individual battery cells, the control unit comprises a battery management system for the battery pack, and the control unit is further configured to determine a state of health of the battery pack based on the signal from the ultrasound sensor.

2. The health monitoring device of claim 1, wherein said battery cell within the battery pack is a lithium-ion battery cell.

3. The health monitoring device of claim 1, wherein the generated and detected ultrasound comprises one or more ultrasonic pulses having a frequency greater than 1 MHz.

4. The health monitoring device of claim 1, further comprising:
   a second sensor configured to measure battery cell internal resistance, battery cell discharge profile, battery cell charging time, battery cell current or voltage, battery cell temperature, battery cell strain, battery cell dimensions, or gas venting from the battery cell and to generate a measurement signal responsively thereto.

5. The health monitoring device of claim 1, wherein said battery cell within the battery pack is a lithium-ion battery cell with multiple electrode layers, the ultrasound source being arranged so as to direct the generated ultrasound perpendicular to a plane of one or more of the electrode layers.

6. The health monitoring device of claim 1, wherein the ultrasound source and the ultrasound sensor are on a same side of the energy storage device.

7. The health monitoring device of claim 6, wherein the ultrasound sensor is configured to detect ultrasound reflected from the energy storage device.

8. The health monitoring device of claim 1, wherein a couplant is disposed along a path of the ultrasound and in contact with an external surface of the energy storage device, and the couplant comprises hydrocarbon grease, an encapsulated gel, or a gel pad.

9. The health monitoring device of claim 1, wherein the energy storage device comprises multiple electrode layers therein, and the ultrasound source is arranged to directed the generated ultrasound at a nonorthogonal angle with respect to a plane of one or more of the multiple electrode layers.

10. A health monitoring device comprising:
an ultrasound source configured to generate and direct ultrasound at an energy storage device;
an ultrasound sensor configured to detect ultrasound reflected from or transmitted through the energy storage device and to generate a signal responsive to the detected ultrasound from the energy storage device;
a control unit that receives the signal from the ultrasound sensor, the control unit being configured to determine a state of health of the energy storage device responsive to said signal;
a testing platform comprising the ultrasound source and the ultrasound sensor; and
a selection device that selects individual energy storage devices from a plurality of energy storage devices for respective assessment by the ultrasound source and the ultrasound sensor of the testing platform,
wherein the control unit is configured to control the ultrasound source and the ultrasound sensor to perform an A-scan and to determine the state of health based on amplitude of the detected ultrasound and timing of the detected ultrasound,
wherein the selection device comprises a conveying system that moves the individual energy storage devices from the plurality of energy storage devices to the testing platform for the respective assessment, and
wherein the control unit controls the conveying system to direct energy storage devices from the testing platform responsive to the determined state of health from the respective assessment.

11. A battery system with state of health monitoring, the battery system comprising:
a battery pack comprising a plurality of individual lithium-ion battery cells;
one or more ultrasonic health monitoring devices, each ultrasonic health monitoring device being arranged to assess one of the lithium-ion battery cells, each ultrasonic health monitoring device including an ultrasound source that directs ultrasound at the respective lithium-ion battery cell and an ultrasound sensor that detects ultrasound reflected from or transmitted through the respective lithium-ion battery cell and generates a signal responsive thereto; and
a battery management system configured to receive the signal from each ultrasound sensor and to determine a state of health of the battery pack based at least in part on said signal.

12. The battery system of claim 11, further comprising one or more second sensors, each second sensor being arranged to assess one or more of the lithium-ion battery cells, each second sensor being configured to measure battery cell internal resistance, battery cell discharge profile, battery cell charging time, battery cell current or voltage, battery cell temperature, battery cell strain, battery cell dimensions, or gas venting from the battery cell and to generate a measurement signal responsively thereto.

13. The battery system of claim 11, wherein the battery pack is constructed for use in an automotive vehicle.

* * * * *